(12) United States Patent
Steger et al.

(10) Patent No.: US 10,752,593 B2
(45) Date of Patent: Aug. 25, 2020

(54) COMPOUNDS FOR USE AS THERAPEUTICALLY ACTIVE SUBSTANCES IN THE TREATMENT OF RETINAL DISEASES

(71) Applicant: ENDOGENA THERAPEUTICS, INC., San Francisco, CA (US)

(72) Inventors: Matthias Steger, Zurich (CH); Alex Mueller, Zurich (CH); Bernhard Fasching, Saint-Louis (FR); Daphna Mokady, Toronto (CA)

(73) Assignee: ENDOGENA THERAPEUTICS, INC., San Francisco, CA (US)

( * ) Notice: Subject to any disclaimer, the term of this patent is extended or adjusted under 35 U.S.C. 154(b) by 0 days.

(21) Appl. No.: 16/235,543

(22) Filed: Dec. 28, 2018

(65) Prior Publication Data
US 2020/0207719 A1 Jul. 2, 2020

(51) Int. Cl.
| C07D 233/64 | (2006.01) |
| C07D 213/56 | (2006.01) |
| A61K 9/00 | (2006.01) |
| A61P 27/02 | (2006.01) |

(52) U.S. Cl.
CPC .......... C07D 233/64 (2013.01); A61K 9/0019 (2013.01); A61K 9/0048 (2013.01); A61P 27/02 (2018.01); C07D 213/56 (2013.01)

(58) Field of Classification Search
CPC ............................. C07D 233/64; C07D 213/56
USPC ....................................................... 514/351
See application file for complete search history.

(56) References Cited

U.S. PATENT DOCUMENTS

| 6,066,675 | A | 5/2000 | Wen et al. |
| 6,117,675 | A | 9/2000 | van der Kooy et al. |
| 2015/0290215 | A1 | 10/2015 | Kusari et al. |
| 2016/0213671 | A1 | 7/2016 | Ueffing et al. |

FOREIGN PATENT DOCUMENTS

| WO | 2001/039792 A2 | 6/2001 |
| WO | 2009/075874 A1 | 6/2009 |
| WO | 2013/016252 A1 | 1/2013 |
| WO | 2013/029338 A1 | 3/2013 |
| WO | 2014/079850 A1 | 5/2014 |
| WO | 2016/073931 A1 | 5/2016 |

OTHER PUBLICATIONS

U.S. Appl. No. 15/946,469, filed Apr. 5, 2018 in the name of Matthias Steger et al.
Loewenstein et al., "Outer Retinal Degeneration, An Electronic Retinal Prosthesis as a Treatment Strategy," Arch Ophthalmol, vol. 122, pp. 587-596, 2004.
Dec. 28, 2018 Office Action issued in U.S. Appl. No. 15/946,469.
May 8, 2019 Office Action issued in U.S. Appl. No. 15/946,469.
Mar. 11, 2020 International Search Report issued in International Patent Application No. PCT/US2019/068759.

*Primary Examiner* — Kahsay Habte
(74) *Attorney, Agent, or Firm* — Oliff PLC

(57) ABSTRACT

A method of treating a retinal disease that leads to photoreceptor loss or outer-retina degeneration, includes administering a compound of formula (Ia) or a pharmaceutically acceptable salt thereof to a patient having the retinal disease so as to be delivered to an eye of the patient in an amount effective to treat the retinal disease:

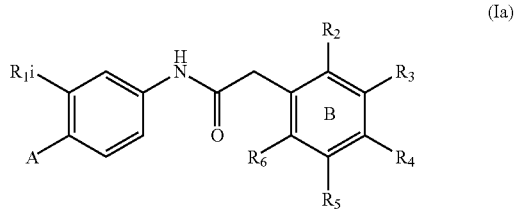

(Ia)

wherein A is an 5-oxazolyl residue or a pyridine-4-yl residue, $R_1$ is selected from the group consisting of methoxy, fluoro and chloro; $R_2$, $R_3$, $R_4$, $R_5$ and $R_6$ of the phenyl ring B are independently from each other selected from the group consisting of hydrogen, a linear or branched alkyl having 1 to 4 carbon atoms, trifluoromethyl, 2,2,2-trifluoroethyl, methylsulfanyl, ethylsulfanyl, methylsulfonyl, ethylsulfonyl, difluoromethoxy, trifluoromethoxy, fluoro, bromo, chloro, methoxy, ethoxy, propoxy, butoxy, hydroxy and amino; and at least two of $R_2$, $R_3$, $R_4$, $R_5$ and $R_6$ are hydrogens.

38 Claims, No Drawings

COMPOUNDS FOR USE AS THERAPEUTICALLY ACTIVE SUBSTANCES IN THE TREATMENT OF RETINAL DISEASES

BACKGROUND

The present application relates to compounds for use as therapeutically active substances in the treatment of retinal diseases, and in particular in the treatment of retinal diseases leading to photoreceptor loss or degeneration of the outer retina.

The main feature of neurodegenerative diseases is an increasing loss of nerve cells, resulting in various neurological symptoms. The diseases can arise in different periods of life, which proceed diffusely or generalized and produce specific patterns of damage.

Of particular importance are neurodegenerative diseases of the eye. The retinal degeneration is a decay of the retina, which can finally result in the death of the cells of the retina. One of the most important forms of the retina degeneration is the so-called retinitis pigmentosa (RP) or also referred to as retinopathia pigmentosa. The chief function of the retina is transduction of light into nervous impulses by the rods and the cones. Retinitis pigmentosa is a chronic retinal degeneration where the deterioration is accompanied by abnormal deposits of pigment in the rods of the retina. The disease causes a progressive decrease in peripheral vision leading to malfunction of the side vision. Eventually, the person with retinitis pigmentosa can see only straight ahead so that the patient experiences a condition known as "tunnel vision".

The therapeutic strategies for treating loss of vision caused by retinal cell damage vary, but they are all directed to controlling the illness causing the damage rather than reversing the damage caused by an illness by restoring or regenerating retinal cells.

WO 2016/073931 discloses a method for the treatment of retinitis pigmentosa in a human that comprises administering to the human a therapeutically effective amount of N-acetylcysteine amide (NACA) which reduces cone cell death in the eye.

EP 2 734 202 discloses a pharmaceutical composition containing 4-bromo-N-(imidazolidin-2-ylidene)-1H-benzimidazol-5-amine as active ingredient for modulating the alpha 2 adrenergic receptors. It was shown that said compound reduced and protected the retina from the damage caused by blue light.

US 2015/290215 discloses a composition comprising clozapine, n-desmethyl clozapine, olanzapine or derivatives thereof for treating a retinal disorder, which is caused by oxidative stress.

US 2016/0213671 relates to a pharmaceutical composition for the treatment or prophylaxis of a neurodegenerative disease, which is not based on a protein-folding disorder comprising as the active agent an inhibitor of the valosin-containing protein (VCP inhibitor).

WO 2014/079850 discloses both substituted heterocyclic compounds which were believed to stimulate adult neuronal stem cells and that said compounds may be used for a plurality of different diseases. However, although neuronal stem cells have the ability to differentiate into several cell types, it cannot be predicted whether said new cell types can be stimulated by the same compounds. However, a significant number of compounds which stimulate neuronal stem cells have no or only a weak activity with regard to other cell types such as retinal precursor cells.

U.S. Pat. No. 6,117,675 discloses stem cells isolated from the retina of mammals and retinal cells differentiated from these stem cells and a method for obtaining cells from a retinal pigment epithelial layer of a mammal.

There is currently no way to reverse permanent damage to the retina and restore vision. Drug treatments focus on treating the illness and its symptoms to prevent further damage to the retina. There is a need to reverse damage to the retina and restore vision by endogenously generating new retinal cells or transplanting retinal cells.

DETAILED DESCRIPTION

The term "precursor cells" encompasses in this context any form of proliferative and non-proliferative cells such as stem cells per se and progenitor cells that can give rise to further differentiated functional tissues of the eye. Such precursor cells include in particular retinal precursor cells.

A problem addressed by the present application is to provide a new compound, which stimulates the proliferation of retinal precursor cells.

The problem is solved by a compound of formula (I). Further preferred embodiments are the subject of the dependent claims.

It has been shown that a compound of formula (I) stimulates production of mammalian retinal precursor cells. The selective activation of the endogenous precursor cells allows a controlled repair and regeneration of the retina. Thus, it is possible to restore vision by endogenously generating new precursor cells by a compound according to the present application. Therefore, the compound is useful as a therapeutically active substance in the treatment of retinal diseases, i.e., as a medicament.

Thus, the present application relates to a compound of formula (I)

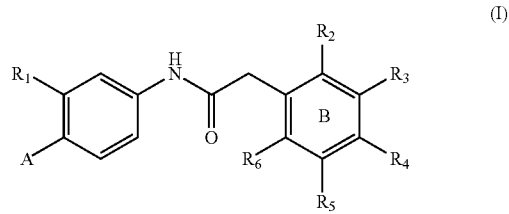

or a pharmaceutically acceptable salt thereof,
wherein:
A is a 5-oxazolyl residue or a pyridine-4-yl residue
$R_1$ is selected from the group consisting of fluoro and chloro; $R_2$, $R_3$, $R_4$, $R_5$ and $R_6$ of the phenyl ring B are independently from each other selected from the group consisting of hydrogen, a linear or branched alkyl having 1 to 4 carbon atoms, trifluoromethyl, 2,2,2-trifluoroethyl, methylsulfanyl, ethylsulfanyl, methylsulfonyl, ethylsulfonyl, difluoromethoxy, trifluoromethoxy, fluoro, bromo, chloro, methoxy, ethoxy, propoxy, butoxy, hydroxy and amino; and at least two of $R_2$, $R_3$, $R_4$, $R_5$ and $R_6$ are hydrogens, with the proviso that if $R_1$ is chloro, $R_5$ is not methoxy.

The term "pharmaceutically acceptable salt" stands for therapeutically active, non-toxic acid salt forms, which the compound according to the present application is able to form.

The term "alkyl" as a group refers to a straight or branched hydrocarbon chain containing 1 to 4 of carbon atoms. Examples of "alkyl" as used herein include methyl, ethyl, n-propyl, isopropyl, n-butyl, isobutyl, sec-butyl and tert-butyl.

The residue A may be a 5-oxazolyl group of the formula (II)

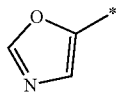

(II)

wherein "*" denotes the point of attachment to the remainder of the molecule.

Alternatively, the residue A may be a pyridine group of the formula (III)

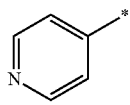

(III)

wherein "*" denotes the point of attachment to the remainder of the molecule.

Preferably, the phenyl ring B in the compound of the present application is monosubstituted or disubstituted, but it is also possible that all of $R_2$, $R_3$, $R_4$, $R_5$ and $R_6$ are hydrogen. The term "monosubstituted" means that one of $R_2$, $R_3$, $R_4$, $R_5$ and $R_6$ is not hydrogen. The term "disubstituted" means that two of $R_2$, $R_3$, $R_4$, $R_5$ and $R_6$ are not hydrogens.

Preferably, in the compound of the present application, $R_1$ is chloro. Said compounds show an outstanding biological activity.

In one embodiment of the present application, $R_1$ is a residue as defined above and the phenyl ring B is not substituted, that is, all of $R_2$, $R_3$, $R_4$, $R_5$ and $R_6$ are hydrogens.

In another embodiment of the present application, $R_1$ is a residue as defined above and the phenyl ring B is monosubstituted, that is, one of $R_2$, $R_3$, $R_4$, $R_5$ and $R_6$ is not hydrogen.

If the phenyl ring B is monosubstituted, $R_2$ is preferably selected from the group consisting of methyl, trifluoromethyl, methylsulfanyl, methylsulfonyl, difluoromethoxy, fluoro, bromo, chloro, methoxy, and ethoxy, most preferably difluoromethoxy and chloro, and $R_2$, $R_3$, $R_4$, $R_5$ and $R_6$ are hydrogen. Such a monosubstituted phenyl ring B with a bulky residue $R_2$ results in a particular good stimulation of retinal precursor cells.

Alternatively, if the phenyl ring B is monosubstituted, $R_2$ is hydrogen and one of $R_3$, $R_4$, $R_5$ and $R_6$ is preferably selected from the group consisting of trifluoromethyl, difluoromethoxy, methoxy, preferably trifluoromethyl and difluoromethoxy.

In another embodiment of the present application, the phenyl ring B is disubstituted, that is, two of $R_2$, $R_3$, $R_4$, $R_5$ and $R_6$ are not hydrogens. The disubstitution may be an ortho, meta or para substitution.

Preferably, $R_2$ is selected from the group consisting of fluoro, bromo and chloro, and one of $R_3$, $R_4$ or $R_5$ is selected from the group consisting of fluoro, bromo and chloro. The two residues which are different from hydrogen may be the same or different from each other. Preferably, $R_2$ is chloro and $R_5$ is fluoro resulting in a para-substitution, or both $R_2$ and $R_4$ are fluoro resulting in a meta-substitution.

Preferably, the compound of formula (I) is selected from the group consisting of compounds of the formula (I), wherein A, $R_1$, $R_2$, $R_3$, $R_4$, $R_5$ and $R_6$ are

TABLE 1

| A | $R_1$ | $R_2$ | $R_3$ | $R_4$ | $R_5$ | $R_6$ |
|---|---|---|---|---|---|---|
| 5-oxazolyl | Cl | Cl | H | H | H | H |
| 5-oxazolyl | Cl | H | Cl | H | H | H |
| 5-oxazolyl | Cl | H | H | Cl | H | H |
| 5-oxazolyl | Cl | H | H | H | Cl | H |
| 5-oxazolyl | Cl | F | H | H | H | H |
| 5-oxazolyl | Cl | H | F | H | H | H |
| 5-oxazolyl | Cl | H | H | F | H | H |
| 5-oxazolyl | Cl | H | H | H | F | H |
| 5-oxazolyl | Cl | Br | H | H | H | H |
| 5-oxazolyl | Cl | H | Br | H | H | H |
| 5-oxazolyl | Cl | H | H | Br | H | H |
| 5-oxazolyl | Cl | H | H | H | Br | H |
| 5-oxazolyl | Cl | $CF_3$ | H | H | H | H |
| 5-oxazolyl | Cl | H | $CF_3$ | H | H | H |
| 5-oxazolyl | Cl | H | H | $CF_3$ | H | H |
| 5-oxazolyl | Cl | H | H | H | $CF_3$ | H |
| 5-oxazolyl | Cl | $OCH_3$ | H | H | H | H |
| 5-oxazolyl | Cl | H | $OCH_3$ | H | H | H |
| 5-oxazolyl | Cl | H | H | $OCH_3$ | H | H |
| 5-oxazolyl | Cl | H | H | H | $OCH_3$ | H |
| 5-oxazolyl | Cl | $CH_3$ | H | H | H | H |
| 5-oxazolyl | Cl | H | $CH_3$ | H | H | H |
| 5-oxazolyl | Cl | H | H | $CH_3$ | H | H |
| 5-oxazolyl | Cl | H | H | H | $CH_3$ | H |
| 5-oxazolyl | Cl | $OCHF_2$ | H | H | H | H |
| 5-oxazolyl | Cl | H | $OCHF_2$ | H | H | H |
| 5-oxazolyl | Cl | H | H | $OCHF_2$ | H | H |
| 5-oxazolyl | Cl | H | H | H | $OCHF_2$ | H |
| 5-oxazolyl | Cl | $SO_2CH_3$ | H | H | H | H |
| 5-oxazolyl | Cl | H | $SO_2CH_3$ | H | H | H |
| 5-oxazolyl | Cl | H | H | $SO_2CH_3$ | H | H |
| 5-oxazolyl | Cl | H | H | H | $SO_2CH_3$ | H |
| 5-oxazolyl | F | Cl | H | H | H | H |
| 5-oxazolyl | F | H | Cl | H | H | H |
| 5-oxazolyl | F | H | H | Cl | H | H |
| 5-oxazolyl | F | H | H | H | Cl | H |
| 5-oxazolyl | F | F | H | H | H | H |
| 5-oxazolyl | F | H | F | H | H | H |
| 5-oxazolyl | F | H | H | F | H | H |
| 5-oxazolyl | F | H | H | H | F | H |
| 5-oxazolyl | F | Br | H | H | H | H |
| 5-oxazolyl | F | H | Br | H | H | H |
| 5-oxazolyl | F | H | H | Br | H | H |
| 5-oxazolyl | F | H | H | H | Br | H |
| 5-oxazolyl | F | $CF_3$ | H | H | H | H |
| 5-oxazolyl | F | H | $CF_3$ | H | H | H |
| 5-oxazolyl | F | H | H | $CF_3$ | H | H |
| 5-oxazolyl | F | H | H | H | $CF_3$ | H |
| 5-oxazolyl | F | $OCH_3$ | H | H | H | H |
| 5-oxazolyl | F | H | $OCH_3$ | H | H | H |
| 5-oxazolyl | F | H | H | $OCH_3$ | H | H |
| 5-oxazolyl | F | H | H | H | $OCH_3$ | H |
| 5-oxazolyl | F | $CH_3$ | H | H | H | H |
| 5-oxazolyl | F | H | $CH_3$ | H | H | H |
| 5-oxazolyl | F | H | H | $CH_3$ | H | H |
| 5-oxazolyl | F | H | H | H | $CH_3$ | H |
| 5-oxazolyl | F | $OCHF_2$ | H | H | H | H |
| 5-oxazolyl | F | H | $OCHF_2$ | H | H | H |
| 5-oxazolyl | F | H | H | $OCHF_2$ | H | H |
| 5-oxazolyl | F | H | H | H | $OCHF_2$ | H |
| 5-oxazolyl | F | $SO_2CH_3$ | H | H | H | H |
| 5-oxazolyl | F | H | $SO_2CH_3$ | H | H | H |
| 5-oxazolyl | F | H | H | $SO_2CH_3$ | H | H |
| 5-oxazolyl | F | H | H | H | $SO_2CH_3$ | H |
| 5-oxazolyl | F | F | H | F | H | H |
| 5-oxazolyl | F | F | H | H | F | H |
| 5-oxazolyl | F | F | H | Cl | H | H |
| 5-oxazolyl | F | F | H | H | Cl | H |
| 5-oxazolyl | Cl | F | H | F | H | H |
| 5-oxazolyl | Cl | F | H | H | F | H |
| 5-oxazolyl | Cl | F | H | Cl | H | H |

TABLE 1-continued

| A | $R_1$ | $R_2$ | $R_3$ | $R_4$ | $R_5$ | $R_6$ |
|---|---|---|---|---|---|---|
| 5-oxazolyl | Cl | F | H | H | Cl | H |
| pyridine-4-yl | Cl | Cl | H | H | H | H |
| pyridine-4-yl | Cl | H | Cl | H | H | H |
| pyridine-4-yl | Cl | H | H | Cl | H | H |
| pyridine-4-yl | Cl | H | H | H | Cl | H |
| pyridine-4-yl | Cl | F | H | H | H | H |
| pyridine-4-yl | Cl | H | F | H | H | H |
| pyridine-4-yl | Cl | H | H | F | H | H |
| pyridine-4-yl | Cl | H | H | H | F | H |
| pyridine-4-yl | Cl | Br | H | H | H | H |
| pyridine-4-yl | Cl | H | Br | H | H | H |
| pyridine-4-yl | Cl | H | H | Br | H | H |
| pyridine-4-yl | Cl | H | H | H | Br | H |
| pyridine-4-yl | Cl | $CF_3$ | H | H | H | H |
| pyridine-4-yl | Cl | H | $CF_3$ | H | H | H |
| pyridine-4-yl | Cl | H | H | $CF_3$ | H | H |
| pyridine-4-yl | Cl | H | H | H | $CF_3$ | H |
| pyridine-4-yl | Cl | $OCH_3$ | H | H | H | H |
| pyridine-4-yl | Cl | H | $OCH_3$ | H | H | H |
| pyridine-4-yl | Cl | H | H | $OCH_3$ | H | H |
| pyridine-4-yl | Cl | $CH_3$ | H | H | H | H |
| pyridine-4-yl | Cl | H | $CH_3$ | H | H | H |
| pyridine-4-yl | Cl | H | H | $CH_3$ | H | H |
| pyridine-4-yl | Cl | H | H | H | $CH_3$ | H |
| pyridine-4-yl | Cl | $OCHF_2$ | H | H | H | H |
| pyridine-4-yl | Cl | H | $OCHF_2$ | H | H | H |
| pyridine-4-yl | Cl | H | H | $OCHF_2$ | H | H |
| pyridine-4-yl | Cl | H | H | H | $OCHF_2$ | H |
| pyridine-4-yl | Cl | $SO_2CH_3$ | H | H | H | H |
| pyridine-4-yl | Cl | H | $SO_2CH_3$ | H | H | H |
| pyridine-4-yl | Cl | H | H | $SO_2CH_3$ | H | H |
| pyridine-4-yl | Cl | H | H | H | $SO_2CH_3$ | H |
| pyridine-4-yl | F | Cl | H | H | H | H |
| pyridine-4-yl | F | H | Cl | H | H | H |
| pyridine-4-yl | F | H | H | Cl | H | H |
| pyridine-4-yl | F | H | H | H | Cl | H |
| pyridine-4-yl | F | F | H | H | H | H |
| pyridine-4-yl | F | H | F | H | H | H |
| pyridine-4-yl | F | H | H | F | H | H |
| pyridine-4-yl | F | H | H | H | F | H |
| pyridine-4-yl | F | Br | H | H | H | H |
| pyridine-4-yl | F | H | Br | H | H | H |
| pyridine-4-yl | F | H | H | Br | H | H |
| pyridine-4-yl | F | H | H | H | Br | H |
| pyridine-4-yl | F | $CF_3$ | H | H | H | H |
| pyridine-4-yl | F | H | $CF_3$ | H | H | H |
| pyridine-4-yl | F | H | H | $CF_3$ | H | H |
| pyridine-4-yl | F | H | H | H | $CF_3$ | H |
| pyridine-4-yl | F | $OCH_3$ | H | H | H | H |
| pyridine-4-yl | F | H | $OCH_3$ | H | H | H |
| pyridine-4-yl | F | H | H | $OCH_3$ | H | H |
| pyridine-4-yl | F | H | H | H | $OCH_3$ | H |
| pyridine-4-yl | F | $CH_3$ | H | H | H | H |
| pyridine-4-yl | F | H | $CH_3$ | H | H | H |
| pyridine-4-yl | F | H | H | $CH_3$ | H | H |
| pyridine-4-yl | F | H | H | H | $CH_3$ | H |
| pyridine-4-yl | F | $OCHF_2$ | H | H | H | H |
| pyridine-4-yl | F | H | $OCHF_2$ | H | H | H |
| pyridine-4-yl | F | H | H | $OCHF_2$ | H | H |
| pyridine-4-yl | F | H | H | H | $OCHF_2$ | H |
| pyridine-4-yl | F | $SO_2CH_3$ | H | H | H | H |
| pyridine-4-yl | F | H | $SO_2CH_3$ | H | H | H |
| pyridine-4-yl | F | H | H | $SO_2CH_3$ | H | H |
| pyridine-4-yl | F | H | H | H | $SO_2CH_3$ | H |
| pyridine-4-yl | F | F | H | F | H | H |
| pyridine-4-yl | F | F | H | H | F | H |
| pyridine-4-yl | F | F | H | Cl | H | H |
| pyridine-4-yl | F | F | H | H | Cl | H |
| pyridine-4-yl | Cl | F | H | F | H | H |
| pyridine-4-yl | Cl | F | H | H | F | H |
| pyridine-4-yl | Cl | F | H | Cl | H | H |
| pyridine-4-yl | Cl | F | H | H | Cl | H |

Especially good results could be obtained by the following compounds according to the present application:

TABLE 2

| Comp. No. | Chemical structure | Cell proliferation within one week [%] |
|---|---|---|
| E0146 | (structure shown) | 203 |
| E0147 | (structure shown) | 142 |
| E0148 | (structure shown) | 143 |

TABLE 2-continued
| Comp. No. | Chemical structure | Cell proliferation within one week [%] |
|---|---|---|
| E0149 | 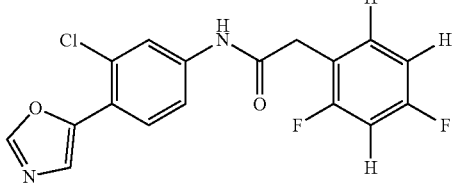 | 157 |
| E1017 | 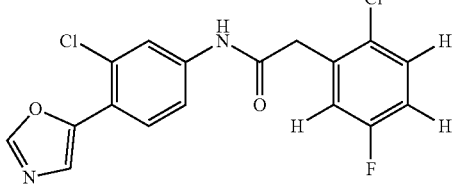 | 121 |
| E1018 | 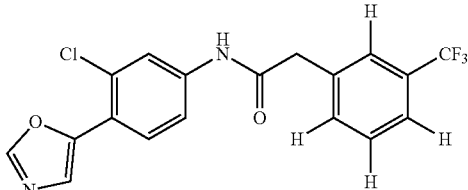 | 134 |
| E1019 | 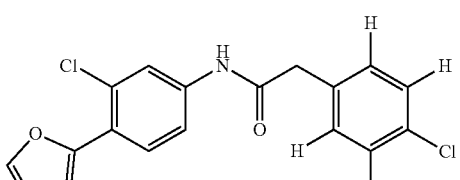 | 133 |
| E1020 | 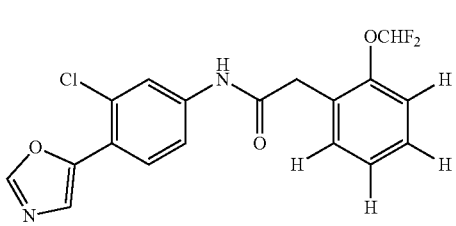 [SMILES: O=C(Cc1ccccc1OC(F)F)Nc1ccc(-c2cnco2)c(Cl)c1] | 135 |
| E1021 | 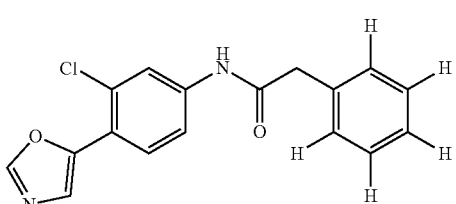 | 149 |
| E1022 | 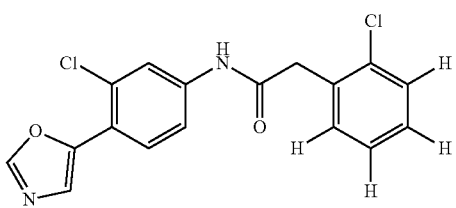 | 158 |

TABLE 2-continued

| Comp. No. | Chemical structure | Cell proliferation within one week [%] |
|---|---|---|
| E1024 | 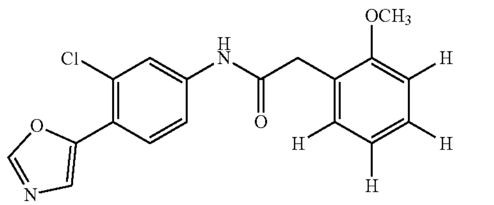 | 128 |
| E1025 | 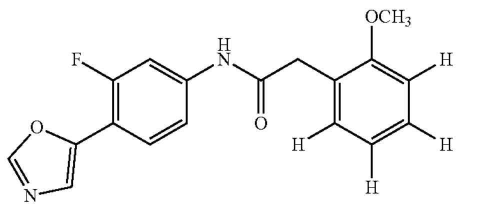 [SMILES: COc1ccccc1CC(=O)Nc1ccc(-c2cnco2)c(F)c1] | 106 |
| E1026 | 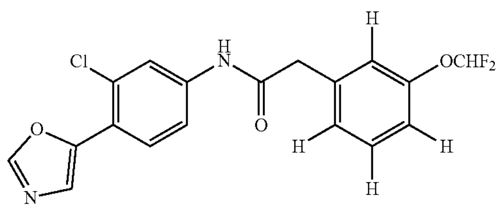 | 122 |
| E1027 | 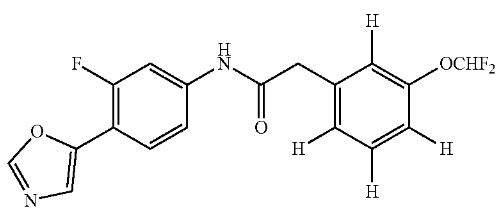 | 120 |
| E1028 | 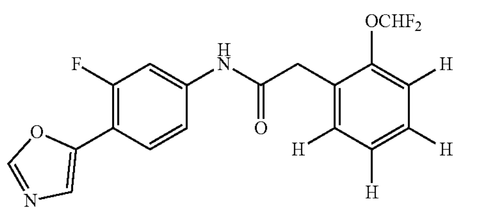 | 119 |
| E1030 | 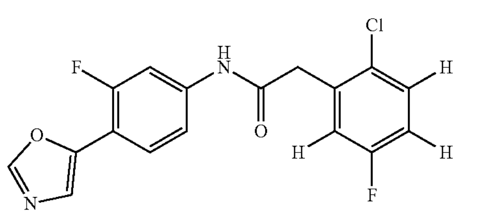 [SMILES: O=C(Cc1ccccc1)Nc1ccc(-c2cnco2)c(F)c1] | 133 |
| E1031 | 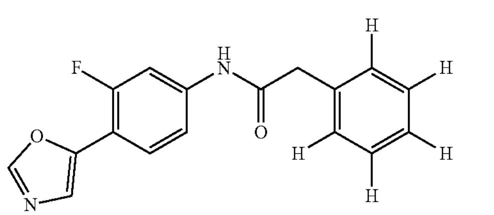 | 123 |

TABLE 2-continued

| Comp. No. | Chemical structure | Cell proliferation within one week [%] |
|---|---|---|
| E1032 | (structure) | 137 |
| E1039 | (structure) | 107 |
| E1042 | (structure) | 127 |
| E1045 | (structure) | 140 |
| E1048 | (structure) | 105 |
| E1051 | (structure) | 118 |
| C* | — | 100 |

C* = Control experiment (absence of a compound according to the present application)

In particular, the compounds of formula (E0146), (E1022), (E0149), (E1021), (E0148) and (E0147) show excellent results with regard to the stimulation of precursor cells, and in particular of retinal precursor cells. Within one week, the compound of formula (E0146) showed an increase of cell proliferation of 103%, the compound of formula (E1022) of 58%, compound of formula (E0149) of 57%, compound of formula (E1021) of 49%, compound of formula (E0148) of 43%, and compound of formula (E0147) of 42%.

In a further embodiment, the present application relates to a pharmaceutical composition comprising a pharmaceutically acceptable carrier and/or adjuvant; and a compound of the formula (Ia)

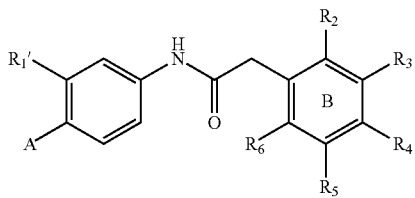

(Ia)

or a pharmaceutically acceptable salt thereof, wherein
A is a 5-oxazolyl residue or a pyridine-4-yl residue
$R_{1'}$ is selected from the group consisting of methoxy, hydrogen, fluoro and chloro;
$R_2$, $R_3$, $R_4$, $R_5$ and $R_6$ of the phenyl ring B are independently from each other selected from the group consisting of hydrogen, a linear or branched alkyl having 1 to 4 carbon atoms, trifluoromethyl, 2,2,2-trifluoroethyl, methylsulfanyl, ethylsulfanyl, methylsulfonyl, ethylsulfonyl, difluoromethoxy, trifluoromethoxy, fluoro, bromo, chloro, methoxy, ethoxy, propoxy, butoxy, hydroxy and amino; and at least two of $R_2$, $R_3$, $R_4$, $R_5$ and $R_6$ are hydrogens,
with the proviso that if $R_{1'}$ is hydrogen or methoxy, A is a pyridine-4-yl residue, as a therapeutically active substance.

The definition of the compound of formula (Ia) differs from the definition of the compound of formula (I) in that $R_{1'}$ is selected from the group consisting of methoxy, hydrogen, fluoro and chloro instead of $R_1$ that was only selected from the group consisting of fluoro and chloro.

The term "pharmaceutical composition" as used here means a composition that is suitable for administering to human patients for the treatment of diseases. Said pharmaceutical composition efficiently stimulates proliferation, migration or both proliferation and migration of endogenous retinal precursor cells in a patient.

In a preferred embodiment of the present application, the pharmaceutical composition comprises a pharmaceutically acceptable carrier and/or adjuvant; and a compound of the formula (I) as defined above, and in particular a compound of formula (I) as disclosed in Table 1 and/or Table 2.

In another embodiment of the present application, the pharmaceutical composition comprises the compound of formula (Ia), wherein $R_1$, $R_2$, $R_3$, $R_4$, $R_5$ and $R_6$ are

TABLE 3

| A | $R_1$ | $R_2$ | $R_3$ | $R_4$ | $R_5$ | $R_6$ |
|---|---|---|---|---|---|---|
| pyridine-4-yl | $OCH_3$ | Cl | H | H | H | H |
| pyridine-4-yl | $OCH_3$ | H | Cl | H | H | H |
| pyridine-4-yl | $OCH_3$ | H | H | Cl | H | H |
| pyridine-4-yl | $OCH_3$ | H | H | H | Cl | H |
| pyridine-4-yl | $OCH_3$ | F | H | H | H | H |
| pyridine-4-yl | $OCH_3$ | H | F | H | H | H |
| pyridine-4-yl | $OCH_3$ | H | H | F | H | H |
| pyridine-4-yl | $OCH_3$ | H | H | H | F | H |
| pyridine-4-yl | $OCH_3$ | Br | H | H | H | H |
| pyridine-4-yl | $OCH_3$ | H | Br | H | H | H |
| pyridine-4-yl | $OCH_3$ | H | H | Br | H | H |
| pyridine-4-yl | $OCH_3$ | H | H | H | Br | H |
| pyridine-4-yl | $OCH_3$ | $CF_3$ | H | H | H | H |
| pyridine-4-yl | $OCH_3$ | H | $CF_3$ | H | H | H |
| pyridine-4-yl | $OCH_3$ | H | H | $CF_3$ | H | H |
| pyridine-4-yl | $OCH_3$ | H | H | H | $CF_3$ | H |
| pyridine-4-yl | $OCH_3$ | $OCH_3$ | H | H | H | H |
| pyridine-4-yl | $OCH_3$ | H | $OCH_3$ | H | H | H |
| pyridine-4-yl | $OCH_3$ | H | H | $OCH_3$ | H | H |
| pyridine-4-yl | $OCH_3$ | H | H | H | $OCH_3$ | H |
| pyridine-4-yl | $OCH_3$ | $CH_3$ | H | H | H | H |
| pyridine-4-yl | $OCH_3$ | H | $CH_3$ | H | H | H |

TABLE 3-continued

| A | $R_1$ | $R_2$ | $R_3$ | $R_4$ | $R_5$ | $R_6$ |
|---|---|---|---|---|---|---|
| pyridine-4-yl | $OCH_3$ | H | H | $CH_3$ | H | H |
| pyridine-4-yl | $OCH_3$ | H | H | H | $CH_3$ | H |
| pyridine-4-yl | $OCH_3$ | $OCHF_2$ | H | H | H | H |
| pyridine-4-yl | $OCH_3$ | H | $OCHF_2$ | H | H | H |
| pyridine-4-yl | $OCH_3$ | H | H | $OCHF_2$ | H | H |
| pyridine-4-yl | $OCH_3$ | H | H | H | $OCHF_2$ | H |
| pyridine-4-yl | $OCH_3$ | $SO_2CH_3$ | H | H | H | H |
| pyridine-4-yl | $OCH_3$ | H | $SO_2CH_3$ | H | H | H |
| pyridine-4-yl | $OCH_3$ | H | H | $SO_2CH_3$ | H | H |
| pyridine-4-yl | $OCH_3$ | H | H | H | $SO_2CH_3$ | H |
| pyridine-4-yl | $OCH_3$ | F | H | F | H | H |
| pyridine-4-yl | $OCH_3$ | F | H | H | F | H |
| pyridine-4-yl | $OCH_3$ | F | H | Cl | H | H |
| pyridine-4-yl | $OCH_3$ | F | H | H | Cl | H |

Especially good results could be obtained by the following compounds according to the present application:

E0027 148

E1060 144

E1062 134

E1063 130

E1066 108

E1068 108

-continued

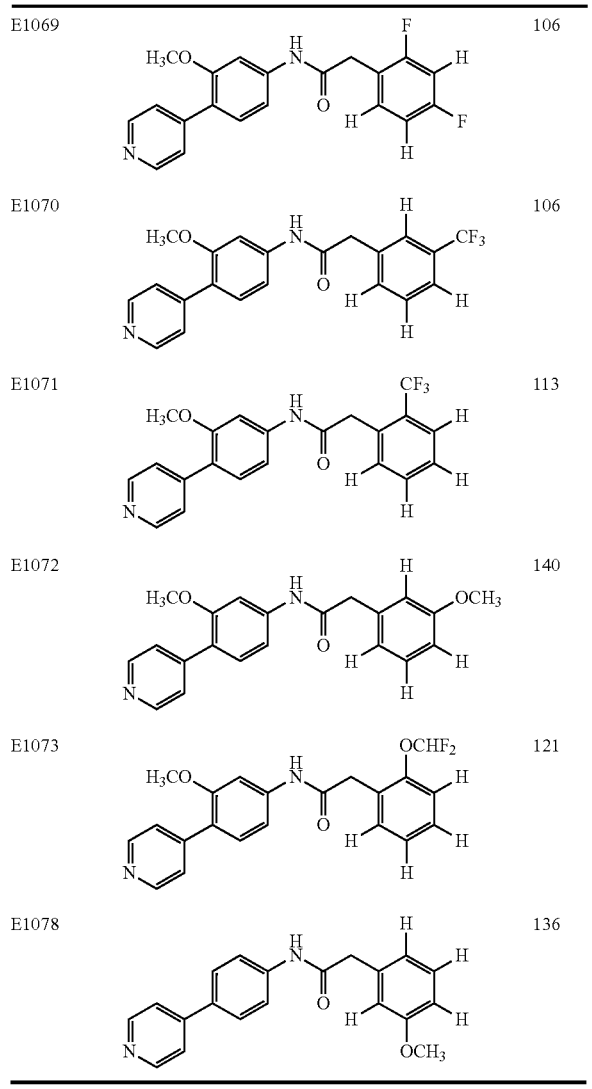

In particular, the compounds of formula (E0027), (E1060) and (E1072) show excellent results with regard to the stimulation of precursor cells, and in particular of retinal precursor cells. Within one week, the compound of formula (E0027) showed an increase of cell proliferation of 48%, the compound of formula (E1060) of 44%, and compound of formula (E1072) of 40%.

As already mentioned, it could be shown that the compounds according to the present application and the composition according to the present application stimulate the proliferation of retinal precursor cells. Thus, they are suitable in the treatment of retinal diseases, in particular of retinal diseases leading to photoreceptor loss or degeneration of the outer retina.

Compounds and compositions according to the present application are particularly useful in the treatment of a disease selected from the group consisting of inherited retinal dystrophies, acquired degeneration, vascular related retinal degeneration, drug-induced maculopathies, infectious eye diseases, inflammatory eye diseases and white dot syndromes, by inducing the proliferation of retinal precursor cells. Thus, due to the compounds and compositions of the present application, it is possible to reverse damage caused by an illness by restoring or regenerating retinal precursor cells, and not only to treat the loss of vision caused by retinal cell damage.

Retinal diseases which may be treated with the compounds according to the present application are preferably selected from the group consisting of retinitis pigmentosa (RP), including syndromic and non-syndromic forms, X-chromosome linked, recessive and dominant forms, rod-cone dystrophies, Usher's syndrome, Stargardt's disease, cone-rod dystrophies, cone dystrophies, achromatopsia, blue cone monochromacy, enhanced S-cone syndrome, rod dystrophies, choroideremia, Leber's congenital amaurosis, juvenile X-chromosome linked retinoschisis (JXLR), Best disease, Gyrate atrophy, fundus albipunctatus, retinitis punctata albescens, fleck retina of Kandori, bietti crystalline retinal dystrophy, North Carolina macular dystrophy, fenestrated sheen macular dystrophy, central areolar choroidal dystrophy (CACD), adult-onset foveomacular vitelliform dystrophy, Batten's disease, familial dominant drusen, congenital stationary night blindness, familial exudative vitreoretinopathy (FEVR), ocular albinism, oculocutaneous albinism, fovea hypoplasia, retinopathy of prematurity, abetalipoproteinemia, Stickler syndrome, retinal dystrophy (Bothnia type), dry age-related macular degeneration (dry AMD), wet age-related macular degeneration (wet AMD), geographic atrophy (GA), myopic degeneration, polypoidal choroidal vasculopathy (PCV), crystalline maculopathy (drug-related, hyperoxaluria, cystinosis, Sjogren-Larsson syndrome), west African crystalline maculopathy, solar retinopathy, talc retinopathy, diabetic retinopathy, sickle cell retinopathy, central serous retinopathy, macular telangectasia, angioid streaks, eales disease, retinal detachment, retinal dialysis, peripheral retinoschisis, central/branch retinal artery occlusion (CRAO/BRAO), central/branch retinal vein occlusion (CRVO/BRVO), haemorrhagic occlusive retinal vasculitis (HORV), drug-induced maculopathies including chloroquine, hydroxychloroquine, phenothiazine, quinine sulfate, thioridazine, clofazimine, cholopromazine, deferoxamine, chloroquine-derivatives, cisplatin, carmustine, chlofazimine and vigabatrin; crystal-induced maculopathies including tamoxifen, talc, canthaxanthine, methoxyflurane and nitrofurantoin; cystoid macular edema (CME) including epinephrine, latanoprost, nicotinic acid; progressive outer retinal necrosis (PORN), acute retinal necrosis (ARN), CMV-retinitis, Sarcoidosis, acute syphilitic posterior placoid chorioretinitis, tuberculosis chorioretinitis, toxoplasmic retinochoroiditis, Vogt-Koyanagi-Harada (VKH), posterior Uveitis and retinal vasculitis, intermediate uveitis, pars planitis+/−CME, enophthalmitis (anterior and/or posterior), posterior scleritis, masquerade syndromes, acute posterior multifocal placoid pigment epitheliopathy (APMPPE), relentless placoid chorioretinopathy (RPC), serpiginous choroiditis, multiple evanescence white dot syndrome (MEWDS), multifocal choroiditis and panuveitis (MCP), punctate inner choroidopathy (PIC), birdshot retinochoroidopathy, presumed ocular histoplasmosis syndrome (POHS), acute macular neuroretinopathy (AMN) and acute zonal occult outer retinopathy (AZOOR).

Compounds and compositions according to the present application are suitable for the use in the treatment a disease selected from the group consisting of inherited retinal dystrophies including retinitis pigmentosa (RP), including syndromic and non-syndromic forms, X-chromosome linked, recessive and dominant forms, rod-cone dystrophies, Usher's syndrome, Stargardt's disease, cone-rod dystrophies, cone dystrophies, achromatopsia, blue cone monochromacy, enhanced S-cone syndrome, rod dystrophies, choroideremia, Leber's congenital amaurosis, juvenile X-chromosome linked retinoschisis (JXLR), Best disease, Gyrate atrophy, fundus albipunctatus, retinitis punctata albescens, fleck retina of Kandori, bietti crystalline retinal dystrophy, North Carolina macular dystrophy, fenestrated sheen macular dystrophy, central areolar choroidal dystrophy (CACD), adult-onset foveomacular vitelliform dystrophy, Batten's disease, familial dominant drusen, congenital stationary night blindness, familial exudative vitreoretinopathy (FEVR), ocular albinism, oculocutaneous albinism, fovea hypoplasia, retinopathy of prematurity, abetalipoproteinemia, Stickler syndrome and retinal dystrophy (Bothnia type). Most preferably, the compound of the present application is used in the treatment of retinitis pigmentosa (RP), including syndromic and non-syndromic forms, X-chromosome linked, recessive and dominant forms.

Compounds and compositions according to the present application are suitable for the use in the treatment of acquired degeneration selected from the group consisting of dry age-related macular degeneration (dry AMD), wet age-related macular degeneration (wet AMD), geographic atrophy (GA), myopic degeneration, polypoidal choroidal vasculopathy (PCV), crystalline maculopathy (drug-related, hyperoxaluria, cystinosis, Sjogren-Larsson syndrome), west African crystalline maculopathy, solar retinopathy, talc retinopathy, diabetic retinopathy, sickle cell retinopathy, central serous retinopathy, macular telangectasia, angioid streaks, eales disease, retinal detachment, retinal dialysis, peripheral retinoschisis.

Compounds and compositions according to the present application are suitable for the use in the treatment of vascular related retinal degeneration selected from the group consisting of central/branch retinal artery occlusion (CRAO/BRAO), central/branch retinal vein occlusion (CRVO/BRVO), haemorrhagic occlusive retinal vasculitis (HORV).

Compounds and compositions according to the present application are suitable for the use in the treatment of drug-induced maculopathies selected from the group consisting of chloroquine, hydroxychloroquine, phenothiazine, quinine sulfate, thioridazine, clofazimine, cholopromazine, deferoxamine, chloroquine-derivatives, cisplatin, carmustine, chlofazimine and vigabatrin as well as crystal-induced maculopathies including tamoxifen, talc, canthaxanthine, methoxyflurane, nitrofurantoin, cystoid macular edema (CME) including Epinephrine, latanoprost and nicotinic acid.

Compounds and compositions according to the present application are suitable for the use in the treatment of infectious and/or inflammatory eye diseases selected from the group consisting of progressive outer retinal necrosis (PORN), acute retinal necrosis (ARN), CMV-retinitis, Sarcoidosis, acute syphilitic posterior placoid chorioretinitis, tuberculosis chorioretinitis, toxoplasmic retinochoroiditis, Vogt-Koyanagi-Harada (VKH), posterior Uveitis and retinal vasculitis, intermediate uveitis, pars planitis+/−CME, enophthalmitis (anterior and/or posterior), posterior scleritis and masquerade syndromes.

Compounds and compositions according to the present application are suitable for the use in the treatment of white dot syndromes selected from the group consisting of acute posterior multifocal placoid pigment epitheliopathy (APMPPE), relentless placoid chorioretinopathy (RPC), serpiginous choroiditis, multiple evanescent white dot syndrome (MEWDS), multifocal choroiditis and panuveitis (MCP), punctate inner choroidopathy (PIC), birdshot retinochoroidopathy, presumed ocular histoplasmosis syndrome (POHS), acute macular neuroretinopathy (AMN) and acute zonal occult outer retinopathy (AZOOR).

The compound or the composition according to the present application can be administered to a patient, either alone or in combination with one or more additional therapeutic agents. "Patient" as used herein, includes mammals such as humans, non-human primates, rats, mice, rabbits, hares, dogs, cats, horses, cows and pigs, preferably human.

The pharmaceutical composition according to the present application may comprise one or more additional therapeutic agents.

Preferably, such a pharmaceutical composition provides controlled release properties. The term "controlled release pharmaceutical compositions" herein refers to any composition or dosage form, which comprises the compound of the present application and which is formulated to provide a longer duration of pharmacological response after administration of the dosage form than is ordinarily experienced after administration of a corresponding immediate release composition comprising the same drug in the same amount. Controlled release may be extended up to several months depending on the matrix used. Preferably, the release of the compound according to the present application takes place over a period of up to 12 months, most preferably over a period of up to 6 months. Such a controlled release formulation results in an increased patient comfort and in significant lower costs.

The matrix material used for a pharmaceutical composition according to the present may comprise hydrophobic release controlling agents. It is preferably selected from but not limited to polyvinyl acetate dispersion, ethyl cellulose, cellulose acetate, cellulose propionate (lower, medium or higher molecular weight), cellulose acetate propionate, cellulose acetate butyrate, cellulose acetate phthalate, cellulose triacetate, poly (methyl methacrylate), poly (ethyl methacrylate), poly (butyl methacrylate), poly (isobutyl methacrylate), and poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate), waxes such as beeswax, carnauba wax, paraffin wax, microcrystalline wax, and ozokerite; fatty alcohols such as cetostearyl alcohol, stearyl alcohol, cetyl alcohol and myristyl alcohol, and fatty acid esters such as glyceryl monostearate; glycerol monooleate, acetylated monoglycerides, tristearin, tripalmitin, cetyl esters wax, glyceryl palmitostearate, glyceryl behenate, or hydrogenated vegetable oils.

The compound of the application can be delivered to the eye through a variety of routes, including but not limited to topical application to the eye or by intraocular injection into, for example, the vitreous or subretinal (interphotoreceptor) space; locally by insertion or injection into the tissue surrounding the eye; systemically through an oral route or by subcutaneous, intravenous or intramuscular injection; or via catheter or implant. Most preferably, the compound of the present application is delivered by intraocular injection. The compound of the application can be administered prior to the onset of the condition to prevent its occurrence, such as during eye surgery, immediately after the onset of the pathological condition, or during the occurrence of an acute or protracted condition.

Depending on the intended mode of administration, the compound according to the present application may be incorporated in any pharmaceutically acceptable dosage form, such as for example, liquids, including solutions, suspensions and emulsions, tablets, suppositories, pills, capsules, powders or the like, preferably dosage forms suitable for single administration of precise dosages, or sustained release dosage forms for continuous controlled administration. Most preferred are liquids.

Liquid pharmaceutically administrable dosage forms can be for example a solution, a suspension or an emulsion, preferably a solution comprising a compound of the present application and optional pharmaceutical adjutants in a carrier, such as for example, water, saline, aqueous dextrose, glycerol, ethanol, DMSO and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate and triethanolamine oleate.

The present application also relates to a method of treating a retinal disease that leads to photoreceptor loss or outer-retina degeneration, comprising administering a compound of formula (Ia) or a pharmaceutically acceptable salt thereof to a patient having the retinal disease so as to be delivered to an eye of the patient in an amount effective to treat the retinal disease. The compound of formula (I) is defined above in detail.

Experiments

Synthesis

Preparative high pressure liquid chromatography (HPLC) used to purify reaction mass in the following examples and preparations was effected according to the following method unless modified in specific examples. A Waters auto purification instrument with a YMC Triart C18 (250×21.2 mm, 5μ) column operated at rt with a flow rate of 16 mL/min. Samples were eluted with 20 mM ammonium bicarbonate in water (mobile phase A) and acetonitrile (mobile phase B) and a gradient profile of 70% A and 30% B initially, then 45% A and 55% B in 3 min, adapted to 20% A and 80% B in 20 min, then to 5% A and 95% B in 21 min, which was held constant for 2 min. Pure fractions were concentrated to yield the final product.

Analytical ultra performance liquid chromatography (UPLC) used in the following examples and preparations was effected according to the following method unless modified in specific examples. A Chromegabond WR C18 (3 cm×3.2 mm, 3μ) column operated with a flow rate of 1.5 mL/min. As mobile phases, 0.02% TFA in water (mobile phase C) and 0.02% TFA in CH3CN (mobile phase D) were used in a gradient starting at 90% C and 10% D, changed to 10% C and 90% D in 3.0 min, then to 90% C and 10% D in 4.0 min, which was held constant up to 5.1 min.

Synthesis of Compounds Comprising a 5-Oxazolyl Residue

Intermediate 1

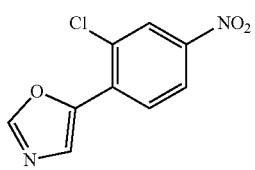 [SMILES: O=[N+]([O-])c1ccc(-c2cnco2)c(Cl)c1]

5-(2-chloro-4-nitrophenyl)oxazole

To a stirred solution of 2-chloro-4-nitrobenzaldehyde (3.00 g, 16.2 mmol) in methanol (20 mL) was added 1-(isocyanomethane)sulfonyl-4-methylbenzene (3.80 g, 19.5 mmol) followed by $K_2CO_3$ (8.00 g, 58.0 mmol) and the reaction mixture was heated to 80° C. and let cool down to rt over 2 h. After completion of the reaction, reaction mass was poured into sat $NaCO_3$ solution (20 mL) and extracted into ethyl acetate (3×200 mL). The organic layer was washed with water, brine, dried over anhydrous sodium sulphate and concentrated under vacuum to get a crude which was purified by column chromatography using silica (100-200) (eluted at 30% ethyl acetate in hexane) to get 5-(2-chloro-4-nitrophenyl)1,3-oxazole (Intermediate 1) (2.9 g, 80%) as yellow solid. LCMS: 225.2 (M+H).

Intermediate 2

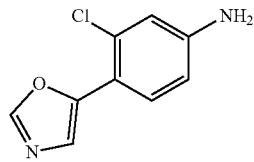

3-chloro-4-(1,3-oxazol-5-yl)aniline

To a stirred solution of 5-(2-chloro-4-nitrophenyl)-1,3-oxazole (Intermediate 1) (3 g, 13.39 mmol) in EtOH (40 mL) were added $SnCl_2$ dihydrate (12.08 g, 53.57 mmol) and conc. HCl (5 mL) dropwise at 0° C. and the reaction mixture was stirred for 30 min at 80° C. After completion of the reaction, the reaction mass was neutralized by 2N NaOH solution and extracted with ethyl acetate (2×50 mL). The organic layer was thoroughly washed with water, dried over anhydrous sodium sulphate and concentrated under vacuum to afford 3-chloro-4-(1,3-oxazol-5-yl)aniline (Intermediate 2) (1.5 g, 57%) as yellow solid. LCMS: 195 (M+H).

Intermediate 3

5-(2-fluoro-4-nitrophenyl)oxazole

To a stirred solution of 2-fluoro-4-nitro benzaldehyde (5 g, 29.56 mmol) and 1-(isocyanomethane)sulfonyl-4-methylbenzene (7.5 g, 38.43 mmol) in MeOH (35 mL) was added K2CO3 (16.3 g, 118.27 mmol) and the reaction mixture was heated to 80° C. for 2 h. After completion of the reaction, reaction mass was poured into saturated $NaHCO_3$ solution (50 mL) and extracted with ethyl acetate (2×50 mL). The organic layer was washed with water, brine, dried over anhydrous sodium sulphate and concentrated under vacuum to get a crude which was purified by column chromatography using silica (100-200) (eluted with 30% ethyl acetate in hexane) to afford 5-(2-fluoro-4-nitrophenyl)-1,3-oxazole (Intermediate 3) (2.5 g, 40%) as yellow solid. LCMS: 209.2 (M+H).

Intermediate 4

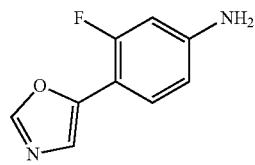 [SMILES: Nc1ccc(-c2cnco2)c(F)c1]

3-fluoro-4-(oxazole-5-yl)aniline

To a stirred solution of 5-(2-fluoro-4-nitrophenyl)-1,3-oxazole (Intermediate 3) (700 mg, 3.36 mmol) in EtOH (35 mL) were added tin(II) chloride SnCl2 dihydrate (3.03 g, 13.46 mmol) and conc. HCl (2 mL) dropwise at 0° C. and the reaction mixture was stirred for 30 min at 80° C. After completion of the reaction, the reaction mass was neutralized with a 2N NaOH solution and extracted with ethyl acetate (2×50 mL). The organic layer was thoroughly washed with water, dried over anhydrous sodium sulphate and concentrated under vacuum to afford 3-fluoro-4-(1,3-oxazol-5-yl)aniline (Intermediate 4) (350 mg, 53%) as yellow solid. LCMS: 179 (M+H).

Synthesis of Compound (E0146)

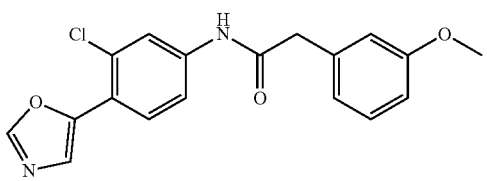 [SMILES: COc1cccc(CC(=O)Nc2ccc(-c3cnco3)c(Cl)c2)c1]

N-(3-chloro-4-(oxazol-5-yl)phenyl)-2-(3-methoxyphenyl)acetamide

To a stirred solution of 3-chloro-4-(oxazole-5-yl)aniline (Intermediate 2) (100 mg, 0.51 mmol) and 2-(3-methoxyphenyl) acetic acid (111 mg, 0.67 mmol) in DMF (1 mL) were added DIPEA (0.26 mL) and HATU (391.9 mg, 1.03 mmol) at rt and the reaction was stirred for 16 h at rt. After completion of the reaction, reaction mass was purified by preparative HPLC to yield N-(3-chloro-4-(oxazol-5-yl)phenyl)-2-(3-methoxyphenyl) acetamide (Compound (E0146)) (46 mg, 26%). Rt: 1.50 min; MS: 343.1 (M+H).

Synthesis of Compound (E0147)

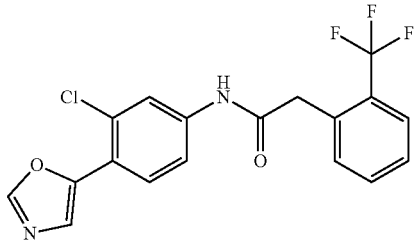 [SMILES: O=C(Cc1ccccc1C(F)(F)F)Nc1ccc(-c2cnco2)c(Cl)c1]

N-(3-chloro-4-(oxazol-5-yl)phenyl)-2-(2-(trifluoromethyl)phenyl)acetamide

To a stirred solution of 3-chloro-4-(oxazole-5-yl)aniline (Intermediate 2) (100 mg, 0.51 mmol) and 2-(2-(trifluoromethyl)phenyl)acetic acid (137 mg, 0.67 mmol) in DMF (1 mL) were added DIPEA (0.26 mL) and HATU (391.9 mg, 1.03 mmol) at rt and the reaction was stirred for 16 h at rt. After completion of the reaction, reaction mass was purified by preparative HPLC to yield N-(3-chloro-4-(oxazol-5-yl)phenyl)-2-(2-(trifluoromethyl)phenyl)acetamide (Compound (E0147)) (68 mg, 35%). Rt: 1.74 min; MS: 381.1 (M+H).

Synthesis of Compound (E0148)

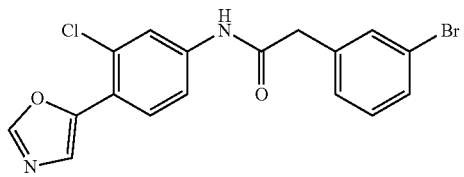 [SMILES: O=C(Cc1cccc(Br)c1)Nc1ccc(-c2cnco2)c(Cl)c1]

2-(3-bromophenyl)-N-(3-chloro-4-(oxazol-5-yl)phenyl) acetamide

To a stirred solution of 3-chloro-4-(oxazole-5-yl)aniline (Intermediate 2) (100 mg, 0.51 mmol) and (2-Chloro-5-fluoro-phenyl)-acetic acid (144 mg, 0.67 mmol) in DMF (1 mL) were added DIPEA (0.26 mL) and HATU (391.9 mg, 1.03 mmol) at rt and the reaction was stirred for 16 h at rt. After completion of the reaction, reaction mass was purified by preparative HPLC to yield 2-(3-bromophenyl)-N-(3-chloro-4-(oxazol-5-yl)phenyl)acetamide (Compound (E0148)) (62 mg, 31%). Rt: 1.77 min; MS: 393.1 (M+H).

Synthesis of compound (E0149)

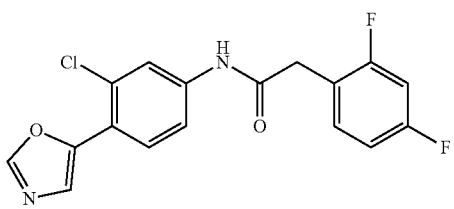 [SMILES: O=C(Cc1ccc(F)cc1F)Nc1ccc(-c2cnco2)c(Cl)c1]

N-(3-chloro-4-(oxazol-5-yl)phenyl)-2-(2,4-difluorophenyl)acetamide

To a stirred solution of 3-chloro-4-(oxazole-5-yl)aniline (Intermediate 2) (100 mg, 0.51 mmol) and (2-Chloro-5-fluoro-phenyl)-acetic acid (115 mg, 0.67 mmol) in DMF (1 mL) were added DIPEA (0.26 mL) and HATU (391.9 mg, 1.03 mmol) at rt and the reaction was stirred for 16 h at rt. After completion of the reaction, reaction mass was purified by preparative HPLC to yield N-(3-chloro-4-(oxazol-5-yl)phenyl)-2-(2,4-difluorophenyl)acetamide (Compound (E0149)) (57 mg, 32%). Rt: 1.59 min; MS: 349.1 (M+H).

Synthesis of Compound (E1017)

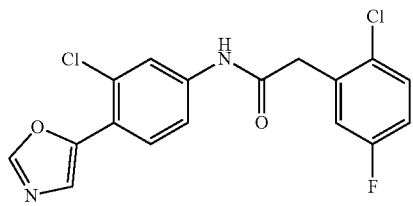 [SMILES: O=C(Cc1cc(F)ccc1Cl)Nc1ccc(-c2cnco2)c(Cl)c1]

N-(3-chloro-4-(oxazol-5-yl)phenyl)-2-(2-chloro-5-fluorophenyl)acetamide

To a stirred solution of 3-chloro-4-(oxazole-5-yl)aniline (Intermediate 2) (100 mg, 0.51 mmol) and (2-Chloro-5-fluoro-phenyl)-acetic acid (126 mg, 0.67 mmol) in DMF (1 mL) were added DIPEA (0.26 mL) and HATU (391.9 mg, 1.03 mmol) at rt and the reaction was stirred for 16 h at rt. After completion of the reaction, reaction mass was purified by preparative HPLC to yield N-(3-chloro-4-(oxazol-5-yl)phenyl)-2-(2-chloro-5-fluorophenyl)acetamide (Compound (E1017)) (34 mg, 18%). Rt: 1.64 min; MS: 365 (M+H).

Synthesis of compound (E1018)

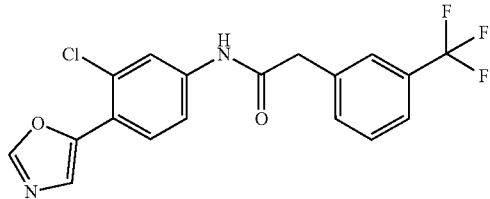 [SMILES: O=C(Cc1cccc(C(F)(F)F)c1)Nc1ccc(-c2cnco2)c(Cl)c1]

N-(3-chloro-4-(oxazol-5-yl)phenyl)-2-(3-(trifluoromethyl)phenyl)acetamide

To a stirred solution of 3-chloro-4-(oxazole-5-yl)aniline (Intermediate 2) (100 mg, 0.51 mmol) and (3-Trifluoromethyl-phenyl)-acetic acid 5(II) (136 mg, 0.67 mmol) in DMF (1 mL) were added DIPEA (0.26 mL) and HATU (392 mg, 1.03 mmol) at rt and the reaction was stirred for 16 h at rt. After completion of the reaction, reaction mass was purified by preparative HPLC to yield N-(3-chloro-4-(oxazol-5-yl)phenyl)-2-(3-(trifluoromethyl)phenyl)acetamide (Compound (E1018)) (26 mg, 13%). Rt: 1.76 min; MS: 381 (M+H).

Synthesis of Compounds Comprising a pyridine-4-yl Residue

Synthesis of Compound (E1019)

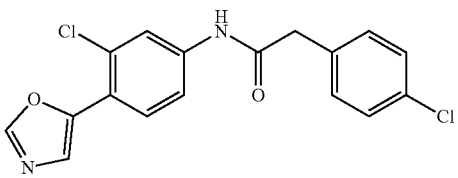 [SMILES: O=C(Cc1ccc(Cl)cc1)Nc1ccc(-c2cnco2)c(Cl)c1]

N-(3-chloro-4-(oxazol-5-yl)phenyl)-2-(4-chlorophenyl) acetamide

To a stirred solution of 3-chloro-4-(oxazole-5-yl)aniline (Intermediate 2) (100 mg, 0.51 mmol) and (4-chloro-phenyl)-acetic acid 5(III) (114 mg, 0.67 mmol) in DMF (1 mL) were added DIPEA (0.26 mL) and HATU (391.9 mg, 1.03 mmol) at rt and the reaction was stirred for 16 h at rt. After completion of the reaction, reaction mass was purified by preparative HPLC to yield N-(3-chloro-4-(oxazol-5-yl)phenyl)-2-(4-chlorophenyl)acetamide (Compound (E1019)) (21 mg, 11%). Rt: 1.68 min; MS: 347.2 (M+H).

Synthesis of Compound (E1020)

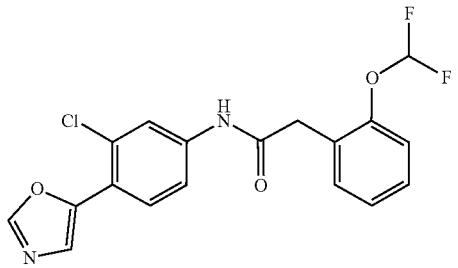 [SMILES: O=C(Cc1ccccc1OC(F)F)Nc1ccc(-c2cnco2)c(Cl)c1]

N-(3-chloro-4-(oxazol-5-yl)phenyl)-2-(2-(difluoromethoxy) phenyl)acetamide

To a stirred solution of 3-chloro-4-(oxazol-5-yl)aniline (Intermediate 2) (150 mg, 0.77 mmol) and 2-(difluoromethoxy) phenyl acetic acid (203 mg, 1 mmol) in DMF (1.5 mL) were added DIPEA (0.39 mL) and HATU (588 mg, 1.55 mmol) at rt and the reaction was stirred for 16 h at rt. After completion of the reaction, reaction mass was purified by preparative HPLC to yield N-(3-chloro-4-(oxazol-5-yl)phenyl)-2-(2-(difluoromethoxy)phenyl)acetamide (Compound (E1020)) (56 mg, 19%). Rt: 1.59 min; MS: 379.2 (M+H).

Synthesis of Compound (E1021)

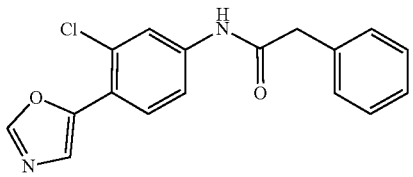 [SMILES: O=C(Cc1ccccc1)Nc1ccc(-c2cnco2)c(Cl)c1]

N-(3-chloro-4-(oxazol-5-yl)phenyl)-2-phenylacetamide

To a stirred solution of 3-chloro-4-(oxazole-5-yl)aniline (Intermediate 2) (150 mg, 0.77 mmol) and phenyl acetic acid (136.85 mg, 1.00 mmol) in DMF (1.5 mL) were added DIPEA (0.39 mL) and HATU (588 mg, 1.55 mmol) at rt and the reaction was stirred for 16 h at rt. After completion of the reaction, reaction mass was purified by preparative HPLC to yield N-(3-chloro-4-(oxazol-5-yl)phenyl)-2-phenylacetamide (Compound (E1021)) (69 mg, 28%). Rt: 1.46 min; MS: 313.2 (M+H).

Synthesis of Compound (E1022)

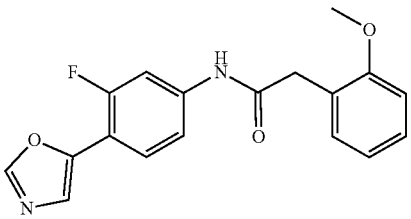

N-(3-chloro-4-(oxazol-5-yl)phenyl)-2-(2-chlorophenyl)acetamide

To a stirred solution of 3-chloro-4-(oxazole-5-yl)aniline (Intermediate 2) (150 mg, 0.77 mmol) and 2-chlorophenylacetic acid (171 mg, 1.00 mmol) in DMF (1.5 mL) were added DIPEA (0.39 mL) and HATU (588 mg, 1.55 mmol) at rt and the reaction was stirred for 16 h at rt. After completion of the reaction, reaction mass was purified by preparative HPLC to yield N-(3-chloro-4-(oxazol-5-yl)phenyl)-2-(2-chlorophenyl)acetamide (Compound (E1022)) (73 mg, 27%). Rt: 1.59 min; MS: 347.1 (M+H).

Synthesis of Compound (E1024)

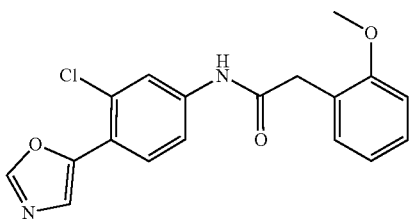 [SMILES: COc1ccccc1CC(=O)Nc1ccc(-c2cnco2)c(Cl)c1]

N-(3-chloro-4-(oxazol-5-yl)phenyl)-2-(2-methoxyphenyl)acetamide

To a stirred solution of 3-chloro-4-(oxazole-5-yl)aniline (Intermediate 2) (150 mg, 0.77 mmol) and 2-methoxyphenylacetic acid (167 mg, 1.00 mmol) in DMF (1.5 mL) were added DIPEA (0.39 mL) and HATU (588 mg, 1.55 mmol) at rt and the reaction was stirred for 16 h at rt. After completion of the reaction, reaction mass was purified by preparative HPLC to yield N-(3-chloro-4-(oxazol-5-yl)phenyl)-2-(2-methoxyphenyl)acetamide (Compound (E1024)) (84 mg, 30%). Rt: 1.48 min; MS: 343.2 (M+H).

Synthesis of compound (E1025)

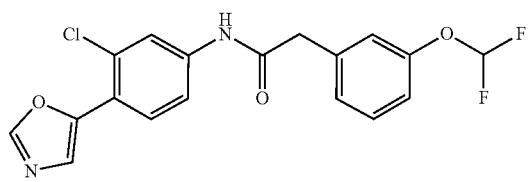

N-(3-fluoro-4-(oxazol-5-yl)phenyl)-2-(2-methoxyphenyl)acetamide

To a stirred solution of 3-fluoro-4-(oxazole-5-yl)aniline (Intermediate 4) (150 mg, 0.84 mmol) and 2-methoxyphenylacetic acid (182 mg, 1.09 mmol) in DMF (1.5 mL) were added DIPEA (0.44 mL) and HATU (640.8 mg, 1.68 mmol) at rt and the reaction was stirred for 16 h at rt. After completion of the reaction, reaction mass was purified by preparative HPLC to yield N-(3-fluoro-4-(oxazol-5-yl)phenyl)-2-(2-methoxyphenyl)acetamide (Compound (E1025)) (93 mg, 33%). Rt: 1.41 min; MS: 327.2 (M+H).

Synthesis of compound (E1026)

N-(3-chloro-4-(oxazol-5-yl)phenyl)-2-(3-(difluoromethoxy)phenyl)acetamide

To a stirred solution of 3-chloro-4-(oxazole-5-yl)aniline (Intermediate 2) (200 mg, 1.03 mmol) and 3-(difluoromethoxy)phenyl acetic acid (270.93 mg, 1.34 mmol) in DMF (2 mL) were added DIPEA (0.52 mL) and HATU (784 mg, 2.06 mmol) at rt and the reaction was stirred for 16 h at rt. After completion of the reaction, reaction mass was purified by preparative HPLC to yield N-(3-chloro-4-(oxazol-5-yl)phenyl)-2-(3-(difluoromethoxy)phenyl)acetamide (Compound (E1026)) (34 mg, 18%). Rt: 1.66 min; MS: 379.2 (M+H).

Synthesis of Compound (E1027)

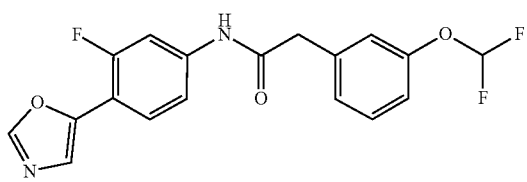 [SMILES: O=C(Cc1cccc(OC(F)F)c1)Nc1ccc(-c2cnco2)c(Cl)c1]

2-(3-(difluoromethoxy)phenyl)-N-(3-fluoro-4-(oxazol-5-yl)phenyl)acetamide

To a stirred solution of 3-fluoro-4-(oxazole-5-yl)aniline (Intermediate 4) (200 mg, 1.12 mmol) and 2-(3-(difluoromethoxy)phenyl)acetic acid (295.3 mg, 1.46 mmol) in DMF (2 mL) were added DIPEA (0.58 mL) and HATU (854.4 mg, 2.24 mmol) at rt and the reaction was stirred for 16 h at rt. After completion of the reaction, reaction mass was purified by preparative HPLC to yield 2-(3-(difluoromethoxy)phenyl)-N-(3-fluoro-4-(oxazol-5-yl)phenyl)acetamide (Compound (E1027)) (104 mg, 25%). Rt: 1.55 min; MS: 363.2 (M+H).

Synthesis of Compound (E1028)

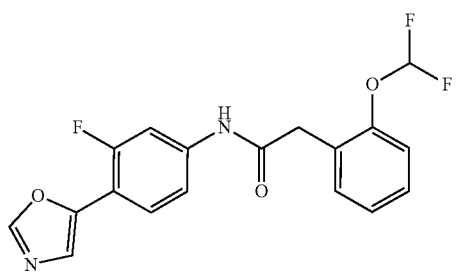 [SMILES: O=C(Cc1ccccc1OC(F)F)Nc1ccc(-c2cnco2)c(F)c1]

2-(2-(difluoromethoxy)phenyl)-N-(3-fluoro-4-(oxazol-5-yl)phenyl)acetamide

To a stirred solution of 3-fluoro-4-(oxazole-5-yl)aniline (Intermediate 4) (200 mg, 1.12 mmol) and 2-(difluoromethoxy)phenyl acetic acid (295.3 mg, 1.46 mmol) in DMF (2 mL) were added DIPEA (0.58 mL) and HATU (854.4 mg, 2.24 mmol) at rt and the reaction was stirred for 16 h at rt. After completion of the reaction, reaction mass was purified by preparative HPLC to yield 2-(2-(difluoromethoxy)phenyl)-N-(3-fluoro-4-(oxazol-5-yl)phenyl)acetamide (Compound (E1028)) (147 mg, 36%). Rt: 1.50 min; MS: 363.2 (M+H).

Synthesis of compound (E1030)

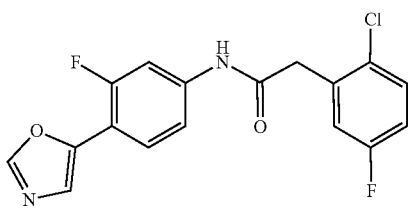

2-(2-chloro-5-fluorophenyl)-N-(3-fluoro-4-(oxazol-5-yl)phenyl)acetamide

To a stirred solution of 3-fluoro-4-(oxazole-5-yl)aniline (Intermediate 4) (200 mg, 1.12 mmol) and (2-Chloro-5-fluoro-phenyl)-acetic acid (275.5 mg, 1.46 mmol) in DMF (2 mL) were added DIPEA (0.58 mL) and HATU (854.4 mg, 2.24 mmol) at rt and the reaction was stirred for 16 h at rt. After completion of the reaction, reaction mass was purified by preparative HPLC to yield 2-(2-chloro-5-fluorophenyl)-N-(3-fluoro-4-(oxazol-5-yl)phenyl)acetamide (Compound (E1030)) (137 mg, 34%). Rt: 1.57 min; MS: 349.2 (M+H).

Synthesis of Compound (E1031)

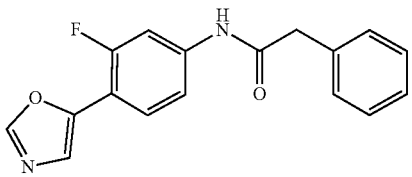 [SMILES: O=C(Cc1ccccc1)Nc1ccc(-c2cnco2)c(F)c1]

N-(3-fluoro-4-(oxazol-5-yl)phenyl)-2-phenylacetamide

To a stirred solution of 3-fluoro-4-(oxazole-5-yl)aniline (Intermediate 4) (100 mg, 0.56 mmol) and 2-phenylacetic acid (99.4 mg, 0.73 mmol) in DMF (1 mL) were added DIPEA (0.29 mL) and HATU (427 mg, 1.12 mmol) at rt and the reaction was stirred for 16 h at rt. After completion of the reaction, reaction mass was purified by preparative HPLC to yield N-(3-fluoro-4-(oxazol-5-yl)phenyl)-2-phenylacetamide (Compound (E1031)) (43 mg, 25%). Rt: 1.36 min; MS: 297.2 (M+H).

Synthesis of compound (E1032)

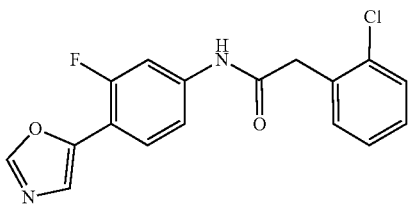 [SMILES: O=C(Cc1ccccc1Cl)Nc1ccc(-c2cnco2)c(F)c1]

2-(2-chlorophenyl)-N-(3-fluoro-4-(oxazol-5-yl)phenyl)acetamide

To a stirred solution of 3-fluoro-4-(oxazole-5-yl)aniline (Intermediate 4) (150 mg, 0.84 mmol) and 2-(2-chlorophenyl)acetic acid (186.9 mg, 1.09 mmol) in DMF (1.5 mL) were added DIPEA (0.44 mL) and HATU (641 mg, 1.68 mmol) at rt and the reaction was stirred for 16 h at rt. After completion of the reaction, reaction mass was purified by preparative HPLC to yield 2-(2-chlorophenyl)-N-(3-fluoro-4-(oxazol-5-yl)phenyl) acetamide (Compound (E1032)) (123 mg, 44%). Rt: 1.50 min; MS: 331.2 (M+H).

Synthesis of Compound (E1039)

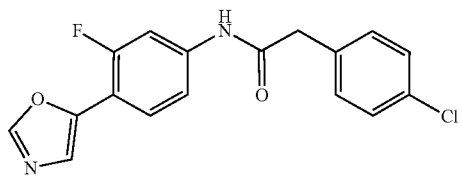 [SMILES: O=C(Cc1ccc(Cl)cc1)Nc1ccc(-c2cnco2)c(F)c1]

2-(4-chlorophenyl)-N-(3-fluoro-4-(oxazol-5-yl)phenyl) acetamide

To a stirred solution of 3-fluoro-4-(oxazole-5-yl)aniline (Intermediate 4) (200 mg, 1.12 mmol) and (4-chloro-phenyl)-acetic acid (249.2 mg, 1.46 mmol) in DMF (2 mL) were added DIPEA (0.58 mL) and HATU (854.4 mg, 2.24 mmol) at rt and the reaction was stirred for 16 h at rt. After completion of the reaction, reaction mass was purified by preparative HPLC to yield 2-(4-chlorophenyl)-N-(3-fluoro-4-(oxazol-5-yl)phenyl)acetamide (Compound (E1039)) (91 mg, 24%). Rt: 1.62 min; MS: 331.2 (M+H).

Synthesis of Compound (E1042)

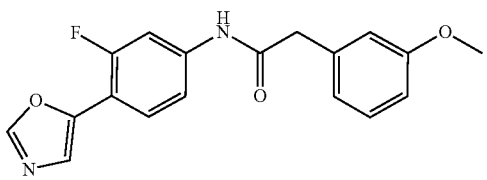 [SMILES: COc1cccc(CC(=O)Nc2ccc(-c3cnco3)c(F)c2)c1]

N-(3-fluoro-4-(oxazol-5-yl)phenyl)-2-(3-methoxyphenyl)acetamide

To a stirred solution of 3-fluoro-4-(oxazole-5-yl)aniline (Intermediate 4) (150 mg, 0.84 mmol) and 3-methoxyphenylacetic acid (182.1 mg, 1.09 mmol) in DMF (1.5 mL) were added DIPEA (0.44 mL) and HATU (641 mg, 1.68 mmol) at rt and the reaction was stirred for 16 h at rt. After completion of the reaction, reaction mass was purified by preparative HPLC to yield N-(3-fluoro-4-(oxazol-5-yl)phenyl)-2-(3-methoxyphenyl)acetamide (Compound (E1042)) (87 mg, 31%). Rt: 1.37 min; MS: 327.2 (M+H).

Synthesis of Compound (E1045)

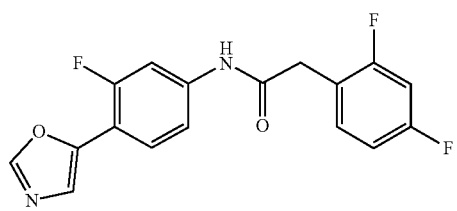 [SMILES: O=C(Cc1ccc(F)cc1F)Nc1ccc(-c2cnco2)c(F)c1]

2-(2,4-difluorophenyl)-N-(3-fluoro-4-(oxazol-5-yl)phenyl)acetamide

To a stirred solution of 3-fluoro-4-(oxazole-5-yl)aniline (Intermediate 4) (150 mg, 0.84 mmol) and 2,4-difluorophenyl acetic acid (188.56 mg, 1.09 mmol) in DMF (1.5 mL) were added DIPEA (0.44 mL) and HATU (641 mg, 1.68 mmol) at rt and the reaction was stirred for 16 h at rt. After completion of the reaction, reaction mass was purified by preparative HPLC to yield to get 2-(2,4-difluorophenyl)-N-(3-fluoro-4-(oxazol-5-yl)phenyl)acetamide (Compound (E1045)) (125 mg, 44%). Rt: 1.52 min; MS: 333.2 (M+H).

Synthesis of Compound (E1048)

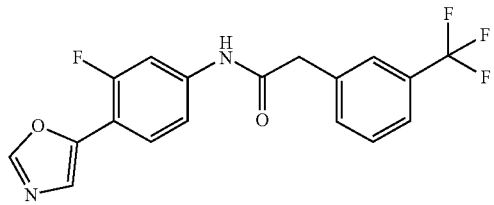 [SMILES: O=C(Cc1cccc(C(F)(F)F)c1)Nc1ccc(-c2cnco2)c(F)c1]

N-(3-fluoro-4-(oxazol-5-yl)phenyl)-2-(3-(trifluoromethyl)phenyl)acetamide

To a stirred solution of 3-fluoro-4-(oxazole-5-yl)aniline (Intermediate 4) (200 mg, 1.12 mmol) and (3-Trifluoromethyl-phenyl)-acetic acid (298.19 mg, 1.46 mmol) in DMF (2 mL) were added DIPEA (0.58 mL) and HATU (854.4 mg, 2.24 mmol) at rt and the reaction was stirred for 16 h at rt. After completion of the reaction, reaction mass was purified by preparative HPLC to yield N-(3-fluoro-4-(oxazol-5-yl)phenyl)-2-(3-(trifluoromethyl)phenyl)acetamide (Compound (E1048)) (137 mg, 33%). Rt: 1.62 min; MS: 365 (M+H).

Synthesis of compound (E1051)

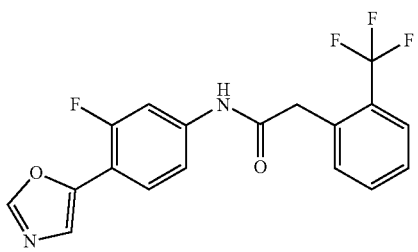

N-(3-fluoro-4-(oxazol-5-yl)phenyl)-2-(2-(trifluoromethyl)phenyl)acetamide

To a stirred solution of 3-fluoro-4-(oxazole-5-yl)aniline (Intermediate 4) (150 mg, 0.84 mmol) and 2-(trifluoromethyl)phenyl acetic acid (223.6 mg, 1.09 mmol) in DMF (1.5 mL) were added DIPEA (0.44 mL) and HATU (641 mg, 1.68 mmol) at rt and the reaction was stirred for 16 h at rt. After completion of the reaction, reaction mass was purified by preparative HPLC to yield to get N-(3-fluoro-4-(oxazol-5- yl)phenyl)-2-(2-(trifluoromethyl)phenyl)acetamide (Compound (E1051)) (125 mg, 40%). Rt: 1.69 min; MS: 365 (M+H).

Intermediate 5

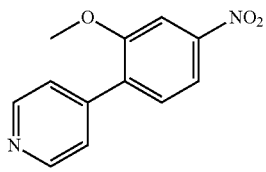

4-(2-methoxy-4-nitrophenyl)pyridine

To a stirred solution of 1-bromo-2-methoxy-4-nitrobenzene (5 g, 21.55 mmol) in 1.4 dioxane (50 ml) and water (10 ml) were added (pyridin-4-yl)boronic acid (3.97 g, 32.32 mmol) and K2CO3 (8.92 g, 64.65 mmol). After degassing with nitrogen for 10 min Pd(Ph3P)4 (0.498 g, 0.431 mmol) was added and the flask was degassed again with nitrogen to then let the reaction mixture be stirred at 85-90° C. for 12 h. After completion of the reaction the reaction mixture was diluted with ethyl acetate (100 ml) followed by washing the ethyl acetate layer with water (2×50 ml) and brine (2×50 ml) successively. The organic layer was dried with Na2SO4 and concentrated to dryness and the crude mass was purified by flash column chromatography, eluted with 15% E.A-Hexane, to afford 4-(2-methoxy-4-nitrophenyl)pyridine (Intermediate 5) (2.5 g, 50.4%) as white solid. LCMS: 230 (M+H).

Intermediate 6

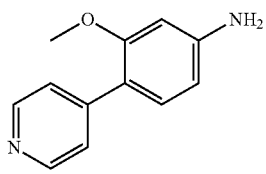

3-methoxy-4-(pyridin-4-yl)aniline

A flask containing 4-(2-methoxy-4-nitrophenyl) pyridine (Intermediate 5) (2.5 g, 10.8 mmol) was flushed with N2 and 10% pd/c (2.3 g, 21.7 mmol) was added. Ethyl acetate (50 mL) was added to the mixture, the N2 supply was replaced with H2 and the black suspension was stirred under H2 for 5 h after which the reaction was completed. The suspension was filtered through celite, washed with ethyl acetate and concentrated under vacuum to yield 3-methoxy-4-(pyridin-4-yl)aniline (Intermediate 6) (1.42 g, 65.2%) as yellow solid. LCMS: 200 (M+H).

Synthesis of compound (E1060)

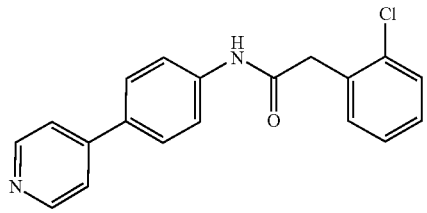 [SMILES: O=C(Cc1ccccc1Cl)Nc1ccc(-c2ccncc2)cc1]

2-(2-chlorophenyl)-N-(4-(pyridin-4-yl)phenyl)acetamide

To a stirred solution of 4-(pyridin-4-yl)aniline (75 mg, 0.441 mmol) and 2-(2-chlorophenyl)acetic acid (112.5 mg, 0.66 mmol) in DMF (3 mL) were added DIPEA (0.169 mL) and HATU (252.7 mg, 0.66 mmol) at rt and the reaction was stirred for 12 h at rt. After completion of the reaction, the reaction mixture was purified by preparative HPLC to yield 2-(2-chlorophenyl)-N-(4-(pyridin-4-yl)phenyl)acetamide (Compound (E1060)) (51.3 mg, 36%). Rt: 0.92 min; MS: 323.2 (M+H).

Synthesis of Compound (E1078)

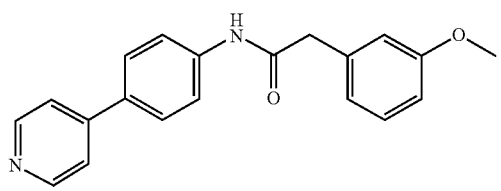 [SMILES: COc1cccc(CC(=O)Nc2ccc(-c3ccncc3)cc2)c1]

2-(3-methoxyphenyl)-N-(4-(pyridin-4-yl)phenyl) acetamide

To a stirred solution of 4-(pyridin-4-yl)aniline (75 mg, 0.441 mmol) and 2-(3-methoxyphenyl)acetic acid (110 mg, 0.66 mmol) in DMF (3 mL) were added DIPEA (0.169 mL) and HATU (252.7 mg, 0.66 mmol) at rt and the reaction was stirred for 12 h at rt. After completion of the reaction, the reaction mixture was purified by preparative HPLC to yield 2-(3-methoxyphenyl)-N-(4-(pyridin-4-yl)phenyl)acetamide (Compound (E1078)) (56 mg, 40%). Rt: 0.86 min; MS: 319.2 (M+H).

Synthesis of compound (E0027)

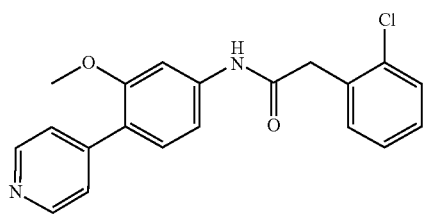 [SMILES: COc1cc(NC(=O)Cc2ccccc2Cl)ccc1-c1ccncc1]

2-(2-chlorophenyl)-N-(3-methoxy-4-(pyridin-4-yl) phenyl) acetamide

To a stirred solution of 3-methoxy-4-(pyridin-4-yl)aniline (Intermediate 6) (75 mg, 0.375 mmol) and 2-(2-chlorophenyl)acetic acid (96 mg, 0.563 mmol) in DMF (2 mL) were added DIPEA (0.144 mL) and HATU (214.8 mg, 0.563 mmol) at rt and the reaction was stirred for 12 h at rt. After completion of the reaction, the reaction mixture was purified by preparative HPLC to yield 2-(2-chlorophenyl)-N-(3-methoxy-4-(pyridin-4-yl)phenyl)acetamide (Compound (E0027)) (20 mg, 15%). Rt: 0.96 min; MS: 353.25 (M+H).

Synthesis of Compound (E1062)

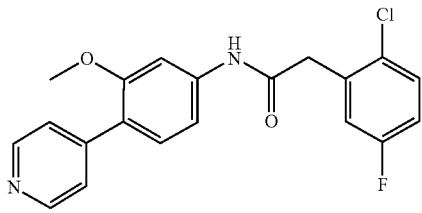 [SMILES: COc1cc(NC(=O)Cc2cc(F)ccc2Cl)ccc1-c1ccncc1]

2-(2-chloro-5-fluorophenyl)-N-(3-methoxy-4-(pyridin-4-yl)phenyl)acetamide

To a stirred solution of 3-methoxy-4-(pyridin-4-yl)aniline (Intermediate 6) (75 mg, 0.375 mmol) and 2-(2-chloro-5-fluorophenyl)acetic acid (105.7 mg, 0.563 mmol) in DMF (2 mL) were added DIPEA (0.144 mL) and HATU (214.8 mg, 0.563 mmol) at rt and the reaction was stirred for 12 h at rt. After completion of the reaction, the reaction mixture was purified by preparative HPLC to yield 2-(2-chloro-5-fluorophenyl)-N-(3-methoxy-4-(pyridin-4-yl)phenyl)acetamide (Compound (E1062)) (69 mg, 50%). Rt: 1.05 min; MS: 371.2 (M+H).

Synthesis of Compound (E1063)

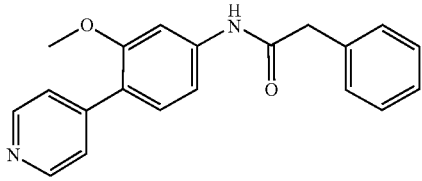 [SMILES: COc1cc(NC(=O)Cc2ccccc2)ccc1-c1ccncc1]

N-(3-methoxy-4-(pyridin-4-yl)phenyl)-2-phenylacetamide

To a stirred solution of 3-methoxy-4-(pyridin-4-yl)aniline (Intermediate 6) (75 mg, 0.375 mmol) and 2-phenylacetic acid (73.1 mg, 0.563 mmol) in DMF (2 mL) were added DIPEA (0.144 mL) and HATU (214.8 mg, 0.563 mmol) at rt and the reaction was stirred for 12 h at rt. After completion of the reaction, the reaction mixture was purified by preparative HPLC to yield N-(3-methoxy-4-(pyridin-4-yl)phenyl)-2-phenylacetamide (Compound (E1063)) (46 mg, 39%). Rt: 0.88 min; MS: 319.2 (M+H).

Synthesis of compound (E1066)

2-(3-(difluoromethoxy)phenyl)-N-(3-methoxy-4-(pyridin-4-yl)phenyl) acetamide

To a stirred solution of 3-methoxy-4-(pyridin-4-yl)aniline (Intermediate 6) (75 mg, 0.375 mmol) and 2-(3-(difluoromethoxy)phenyl)acetic acid (113.6 mg, 0.563 mmol) in DMF (2 mL) were added DIPEA (0.144 mL) and HATU (214.8 mg, 0.563 mmol) at rt and the reaction was stirred for 12 h at rt. After completion of the reaction, the reaction mixture was purified by preparative HPLC to yield 2-(3-(difluoromethoxy)phenyl)-N-(3-methoxy-4-(pyridin-4-yl)phenyl)acetamide (Compound (E1066)) (94 mg, 65%). Rt: 1.10 min; MS: 385.3 (M+H).

Synthesis of compound (E1068)

N-(3-methoxy-4-(pyridin-4-yl)phenyl)-2-(2-methoxyphenyl)acetamide

To a stirred solution of 3-methoxy-4-(pyridin-4-yl)aniline (Intermediate 6) (75 mg, 0.375 mmol) and 2-(2-methoxyphenyl)acetic acid (93.3 mg, 0.563 mmol) in DMF (2 mL) were added DIPEA (0.144 mL) and HATU (214.8 mg, 0.563 mmol) at rt and the reaction was stirred for 12 h at rt. After completion of the reaction, the reaction mixture was purified by preparative HPLC to yield N-(3-methoxy-4-(pyridin-4-yl)phenyl)-2-(2-methoxyphenyl)acetamide (Compound (E1068)) (83 mg, 64%). Rt: 0.93 min; MS: 349.3 (M+H).

Synthesis of compound (E1069)

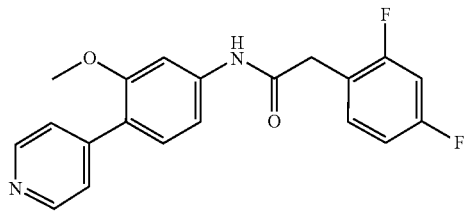 [SMILES: COc1cc(NC(=O)Cc2ccc(F)cc2F)ccc1-c1ccncc1]

2-(2,4-difluorophenyl)-N-(3-methoxy-4-(pyridin-4-yl)phenyl) acetamide

To a stirred solution of 3-methoxy-4-(pyridin-4-yl)aniline (Intermediate 6) (75 mg, 0.375 mmol) and 2-(2,4-difluorophenyl) acetic acid (96.8 mg, 0.563 mmol) in DMF (2 mL) were added DIPEA (0.144 mL) and HATU (214.8 mg, 0.563 mmol) at rt and the reaction was stirred for 12 h at rt. After completion of the reaction, the reaction mixture was purified by preparative HPLC to yield 2-(2,4-difluorophenyl)-N-(3-methoxy-4-(pyridin-4-yl)phenyl) acetamide (Compound (E1069)) (98 mg, 73%). Rt: 0.97 min; MS: 355.2 (M+H).

Synthesis of compound (E1070)

N-(3-methoxy-4-(pyridin-4-yl)phenyl)-2-(3-(trifluoromethyl)phenyl)acetamide

To a stirred solution of 3-methoxy-4-(pyridin-4-yl)aniline (Intermediate 6) (75 mg, 0.375 mmol) and 2-(3-(trifluoromethyl) phenyl) acetic acid (113.7 mg, 0.563 mmol) in DMF (2 mL) were added DIPEA (0.144 mL) and HATU (214.8 mg, 0.563 mmol) at rt and the reaction was stirred for 12 h at rt. After completion of the reaction, the reaction mixture was purified by preparative HPLC to yield N-(3-methoxy-4-(pyridin-4-yl)phenyl)-2-(3-(trifluoromethyl)phenyl)acetamide (Compound (E1070)) (79 mg, 54%). Rt: 1.25 min; MS: 387.3 (M+H).

Synthesis of compound (E1071)

N-(3-methoxy-4-(pyridin-4-yl)phenyl)-2-(2-(trifluoromethyl)phenyl)acetamide

To a stirred solution of 3-methoxy-4-(pyridin-4-yl)aniline (Intermediate 6) (75 mg, 0.375 mmol) and 2-(2-(trifluoromethyl)phenyl)acetic acid (114.9 mg, 0.563 mmol) in DMF (2 mL) were added DIPEA (0.144 mL) and HATU (214.8 mg, 0.563 mmol) at rt and the reaction was stirred for 12 h at rt. After completion of the reaction, the reaction mixture was purified by preparative HPLC to N-(3-methoxy-4-(pyridin-4-yl)phenyl)-2-(2-(trifluoromethyl)phenyl)acetamide (Compound (E1071)) (118 mg, 81%). Rt: 1.13 min; MS: 387.3 (M+H).

Synthesis of compound (E1072)

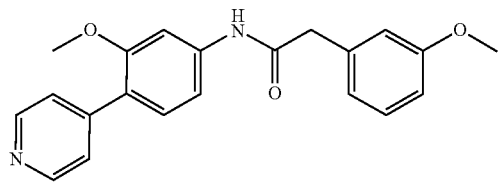 [SMILES: COc1cccc(CC(=O)Nc2ccc(-c3ccncc3)c(OC)c2)c1]

N-(3-methoxy-4-(pyridin-4-yl)phenyl)-2-(3-methoxyphenyl)acetamide

To a stirred solution of 3-methoxy-4-(pyridin-4-yl)aniline (Intermediate 6) (75 mg, 0.375 mmol) and 2-(3-methoxyphenyl)acetic acid (93.3 mg, 0.563 mmol) in DMF (2 mL) were added DIPEA (0.144 mL) and HATU (214.8 mg, 0.563 mmol) at rt and the reaction was stirred for 12 h at rt. After completion of the reaction, the reaction mixture was purified by preparative HPLC to yield N-(3-methoxy-4-(pyridin-4-yl)phenyl)-2-(3-methoxyphenyl)acetamide (Compound (E1072)) (68 mg, 52%). Rt: 0.91 min; MS: 349.3 (M+H).

Preparation of Dissecting Solutions and Enzyme Solutions

Kynurenic Acid (0.2 mg/mL), trypsin (1.33 mg/mL), and hyaluronidase (0.67 mg/mL) were weighed out and dissolved in high magnesium/low calcium artificial cerebral spinal fluid (aCSF) at 37° C. Fibroblast growth factor 2 (FGF2; 10 ng/mL) and heparin (2 µg/mL) were added to 100 mL of serum-free media (SFM). Ovomucoid trypsin inhibitor (1 mg/mL) was dissolved in warm SFM and sterile filtered (22 µm).

Isolation of Retinal Precursor Cells from the Ciliary Epithelium of the Eye and Primary Sphere Assay A dissecting microscope, cold light source, and sterile surgical instruments were set up inside of a sterile biological safety cabinet (BSC). Mammalian eyes were enucleated and placed in a petri dish containing cold, sterile aCSF. Under the dissecting microscope, hair, connective tissue, and the dorsal and ventral oblique muscles were cleared from the scleral/corneal border with two sets of forceps. Next, curved or angled micro-dissecting scissors were used to cleave any remaining extraocular muscle tissue, the optic nerve, and cut the eyeball into symmetrical halves; beginning and finishing the cut from the hole left by the optic nerve. Using two sets of forceps to grasp the cornea, the two eye halves were peeled apart. The lens, optic nerve, and vitreous were separated from the eye shells and the eye shells were transferred into a new petri dish (also containing cold, sterile aCSF). To isolate the ciliary epithelium (CE), eye shells were oriented with the cornea on the right and retinal pigmented epithelium (RPE) on the left. A pair of straight forceps were used to pin down the eye shell on the RPE side while a scalpel blade was inserted between the CE and the iris, using pressure to slice the iris/cornea side off from the rest of the shell. Next, the scalpel was run along the border between the CE and the RPE to obtain the CE isolated as a thin strip of tissue. The CE strips were then transferred to a 35 mm dish containing 2 mL of dispase solution (Sigma; T1005) and incubated for 10 minutes at 37° C. Next, the strips were transferred from dispase into a 35 mm dish containing 2 mL of sterile filtered kynurenic acid, trypsin and hyaluronidase solution and incubated at 37° C. for 10 minutes. After incubation, the dish was returned to the dissecting scope, and the CE strips were pinned down with straight, non-serrated forceps, while non-serrated curved forceps were used to scrape the CE off from the underlying sclera. The bare scleral strips were then discarded, such that only the CE cells remained in the enzyme solution. Using a fire-polished, cotton-plugged glass pipette, the cells and enzyme solution were transferred to a 15 mL tube and triturated approximately 45 times to break apart the tissue. The 15 mL tube/cell suspension was centrifuged for 5 minutes at 1500 rpm. The supernatant was gently aspirated from the resulting pellet using a fire-polished, cotton-plugged glass pipette and 2 mL of trypsin inhibitor solution was added to the pellet. Using a small borehole, fire-polished, cotton-plugged glass pipette, the sample was triturated approximately 45 times until it was a single-cell suspension. The 15 mL tube/cell suspension was centrifuged for 5 minutes at 1500 rpm. The supernatant was gently aspirated from the resulting pellet and 1-2 mL of SFM with FGF2 and heparin (plating media) was added. The cells and media were mixed to ensure a uniform cell suspension and a 10 uL sample was taken and cell density was determined. The cells were then seeded and cultured at 10c/µL in culture-treated plates or flasks. After one week, roughly 1 in 500 cells proliferated to form free-floating, clonal spheres greater than 80 µm in diameter.

Sphere Passaging and High-Throughput Drug Screening

Human-derived spheres were passaged using the kynurenic acid, trypsin, hyaluronidase enzyme solution with the addition of collagenase I (0.5 mg/mL), collagenase II (0.5 mg/mL) and elastase (0.1 mg/mL). Mouse-derived spheres were passaged using hyaluronidase (0.67 mg/mL), collagenase I (0.5 mg/mL), and collagenase II (0.5 mg/mL) dissolved in Accustase solution (Sigma; SCR005). Spheres were collected en masse from culture plates or flasks, transferred into one or more 50 mL tubes and centrifuged for 5 minutes at 1500 rpm. The supernatant was gently aspirated from the pellet and 2-5 mL of enzyme solution was added to the pellet and mixed thoroughly. The 2-5 mL enzyme and sphere suspension was transferred to a 15 mL tube and laid horizontally on an automated rocker at 37° C. for 45 minutes. After incubation, the enzyme solution with spheres was triturated approximately 45 times to mechanically dissociate the spheres. The cell suspension was centrifuged for 5 minutes at 1500 rpm. The supernatant was gently aspirated and 1-2 mL of trypsin inhibitor solution was added to the pellet and triturated approximately 45 times. The cell suspension was centrifuged for 5 minutes at 1500 rpm. The supernatant was gently aspirated from the resulting pellet and 1-2 mL of SFM with FGF2 and heparin (plating media) was added. The cells and media were mixed to ensure a uniform cell suspension and a 10 uL sample was taken and cell density was determined from that sample. The remaining cells were then seeded and cultured at 10c/µL in prepared 96-well or 24-well plates with 0.1% DMSO or a selected concentration of drug in 0.1% DMSO. Cells were grown for one week and then live stained for nuclei (Hoechst 33258; 10 µg/mL). For mouse tissue, an actin-green fluorescent protein (GFP) transgenic mouse strain (FVB.Cg-Tg(CAG-EGFP)B5Nagy/J) was used and cell number comparisons were made based on nuclei and GFP-based quantification. For human tissue, the green fluorescent cell viability dye, calcein AM (ThermoFisher C3100MP; 2 µM) was used and cell number comparisons were made based on nuclei and calcein fluorescence-based quantification.

Statistical evaluation of Drug Screening results Statistical significance was evaluated on a plate to plate basis employing control wells with no drug treatment and equivalent concentration of DMSO in the medium. The minimal number of control wells was 8 for 96 well plates and 6 for 24 well plates. Average and standard deviations were determined and compound wells with cell numbers outside the three standard deviations range around the control value were classified as hits. Individual compound treatment conditions on each plate were always at least present in duplicates to internally verify the validity of results. Numerical values were then averaged for each compound.

Results:

TABLE 2

| Comp. No. | Chemical structure | Cell proliferation within one week [%] |
|---|---|---|
| E0146 | 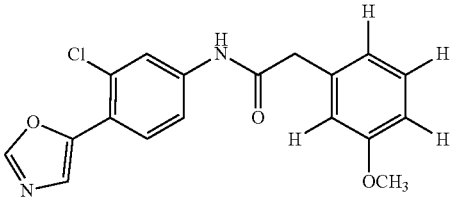 [SMILES: COc1cccc(CC(=O)Nc2ccc(-c3cnco3)c(Cl)c2)c1] | 203 |
| E0147 | 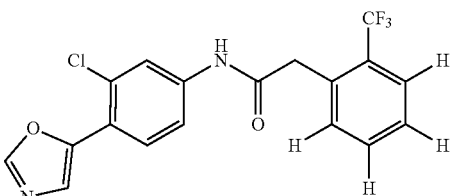 | 142 |
| E0148 | 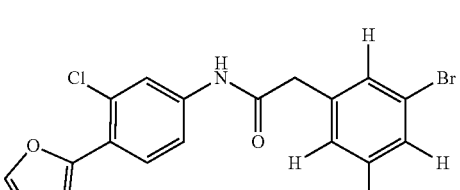 | 143 |
| E0149 | 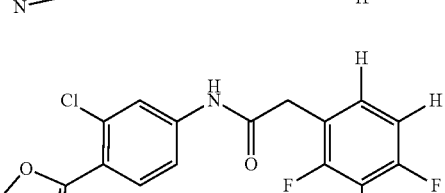 | 157 |
| E1017 | 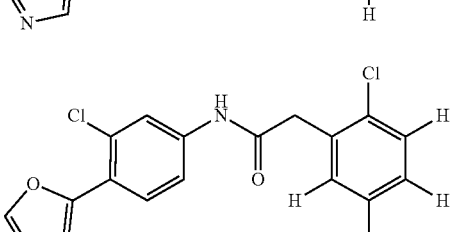 | 121 |

TABLE 2-continued

| Comp. No. | Chemical structure | Cell proliferation within one week [%] |
|---|---|---|
| E1018 | 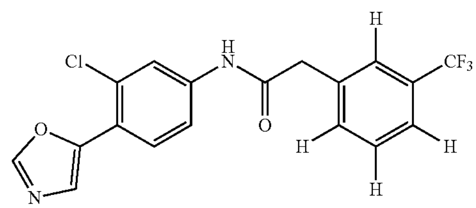 | 134 |
| E1019 | 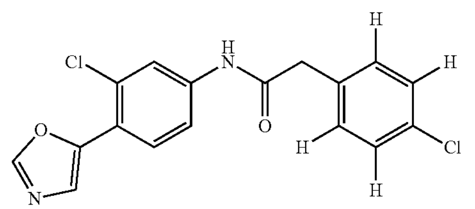 | 133 |
| E1020 | 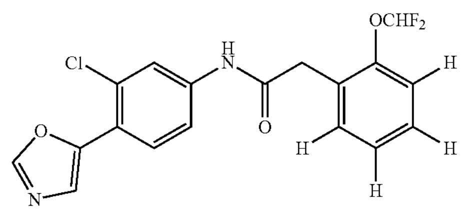 [SMILES: O=C(Cc1ccccc1OC(F)F)Nc1ccc(-c2cnco2)c(Cl)c1] | 135 |
| E1021 | 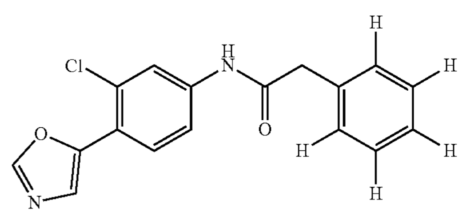 | 149 |
| E1022 | 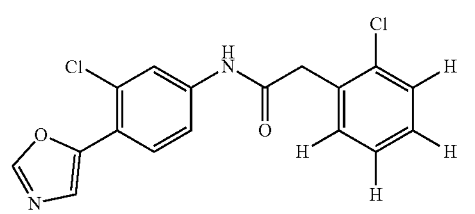 [SMILES: O=C(Cc1ccccc1)Nc1ccc(-c2cnco2)c(Cl)c1] | 158 |
| E1024 | 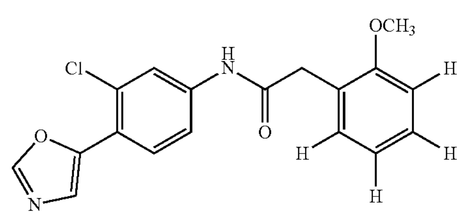 [SMILES: COc1ccccc1CC(=O)Nc1ccc(-c2cnco2)c(Cl)c1] | 128 |
| E1025 | 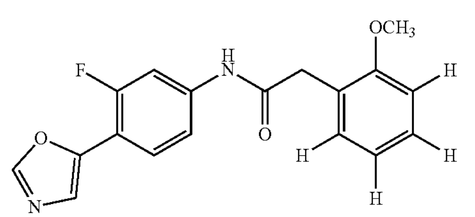 [SMILES: COc1ccccc1CC(=O)Nc1ccc(-c2cnco2)c(F)c1] | 106 |

TABLE 2-continued

| Comp. No. | Chemical structure | Cell proliferation within one week [%] |
|---|---|---|
| E1026 | 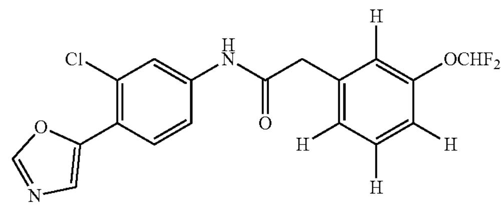 [SMILES: O=C(Cc1cccc(OC(F)F)c1)Nc1ccc(-c2cnco2)c(Cl)c1] | 122 |
| E1027 | 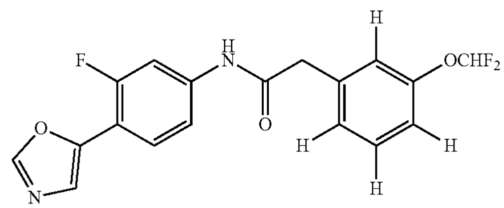 [SMILES: O=C(Cc1cccc(OC(F)F)c1)Nc1ccc(-c2cnco2)c(F)c1] | 120 |
| E1028 | 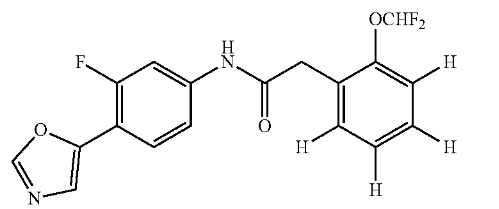 | 119 |
| E1030 | 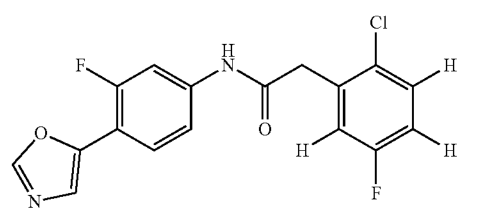 [SMILES: O=C(Cc1cc(F)ccc1Cl)Nc1ccc(-c2cnco2)c(F)c1] | 133 |
| E1031 | 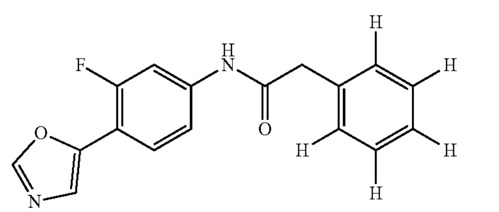 | 123 |
| E1032 | 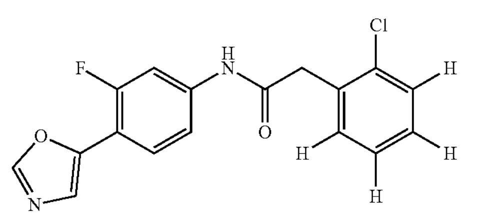 | 137 |
| E1039 | 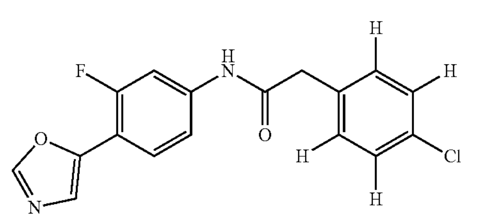 [SMILES: O=C(Cc1ccc(Cl)cc1)Nc1ccc(-c2cnco2)c(F)c1] | 107 |

TABLE 2-continued
| Comp. No. | Chemical structure | Cell proliferation within one week [%] |
|---|---|---|
| E1042 | 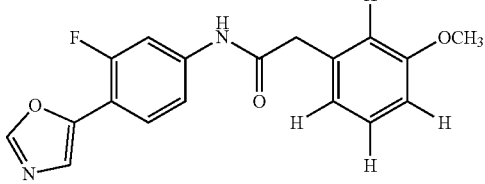 | 127 |
| E1045 | 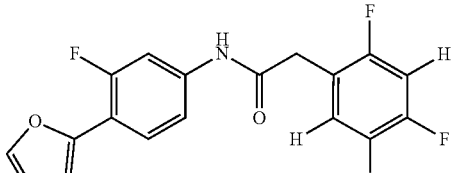 | 140 |
| E1048 | 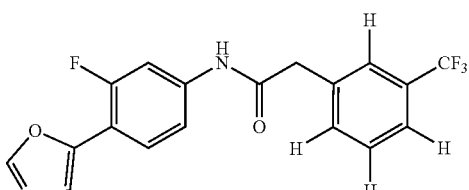 | 105 |
| E1051 | 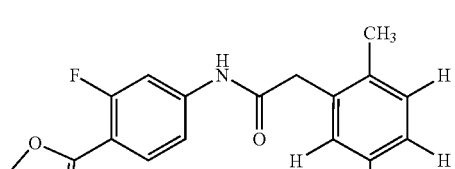 | 118 |
| E0027 | 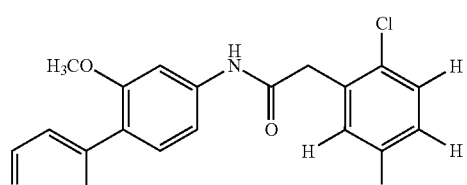 | 148 |
| E1060 | 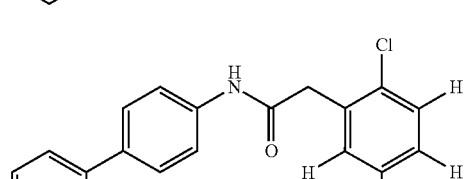 | 144 |
| E1062 | 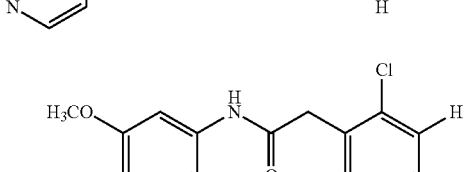 | 134 |

TABLE 2-continued
| Comp. No. | Chemical structure | Cell proliferation within one week [%] |
|---|---|---|
| E1063 | 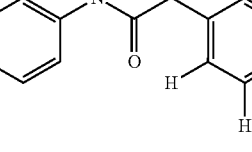 | 130 |
| E1066 | 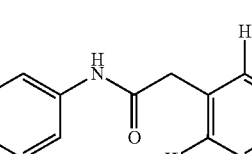 | 108 |
| E1068 | 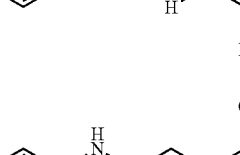 | 108 |
| E1069 | 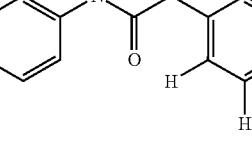 | 106 |
| E1070 | 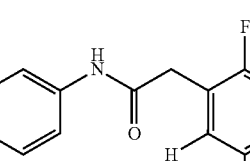 | 106 |
| E1071 | 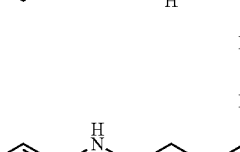 | 113 |
| E1072 | 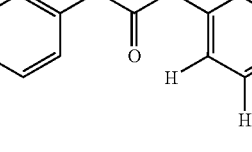 | 140 |

TABLE 2-continued

| Comp. No. | Chemical structure | Cell proliferation within one week [%] |
|---|---|---|
| E1073 | 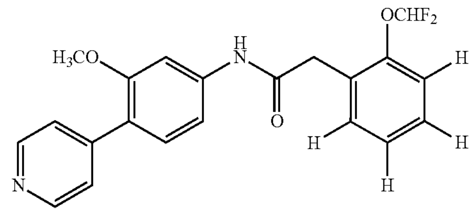 [SMILES: COc1cc(NC(=O)Cc2ccccc2OC(F)F)ccc1-c1ccncc1] | 121 |
| E1078 | 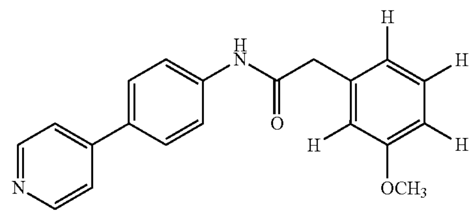 [SMILES: COc1cccc(CC(=O)Nc2ccc(-c3ccncc3)cc2)c1] | 136 |
| C* | — | 100 |

C* = Control experiment (absence of a compound according to the present application

The invention claimed is:

1. A compound of formula (I)

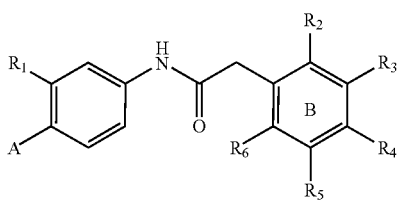

(I)

or a pharmaceutically acceptable salt thereof, wherein:

A is a 5-oxazolyl residue or a pyridine-4-yl residue;

$R_1$ is selected from the group consisting of fluoro and chloro;

$R_2$, $R_3$, $R_4$, $R_5$ and $R_6$ of the phenyl ring B are independently from each other selected from the group consisting of hydrogen, a linear or branched alkyl having 1 to 4 carbon atoms, trifluoromethyl, 2,2,2-trifluoroethyl, methylsulfanyl, ethylsulfanyl, methylsulfonyl, ethylsulfonyl, difluoromethoxy, trifluoromethoxy, fluoro, bromo, chloro, methoxy, ethoxy, propoxy, butoxy, hydroxy and amino; and at least two of $R_2$, $R_3$, $R_4$, $R_5$ and $R_6$ are hydrogens, with the proviso that if $R_1$ is chloro, $R_5$ is not methoxy.

2. The compound according to claim 1, wherein $R_1$ is chloro.

3. The compound according to claim 1, wherein A is a 5-oxazolyl residue.

4. The compound according to claim 1, wherein the phenyl ring B is monosubstituted or disubstituted.

5. The compound according to claim 1, wherein the phenyl ring B is monosubstituted.

6. The compound according to claim 5, wherein $R_2$ is selected from the group consisting of methyl, trifluoromethyl, methylsulfanyl, methylsulfonyl, difluoromethoxy, fluoro, bromo, chloro, methoxy and ethoxy.

7. The compound according to claim 5, wherein $R_2$ is difluoromethoxy or chloro.

8. The compound according to claim 5, wherein $R_3$ or $R_4$ is selected from the group consisting of trifluoromethyl, difluoromethoxy, and methoxy.

9. The compound according to claim 1, wherein the phenyl ring B is disubstituted.

10. The compound according to claim 9, wherein $R_2$ is selected from the group consisting of fluoro, bromo, and chloro, and one of $R_3$, $R_4$ or $R_5$ is selected from the group consisting of fluoro, bromo, and chloro.

11. The compound according to claim 10, wherein $R_2$ is chloro and $R_5$ is fluoro.

12. The compound according to claim 10, wherein both $R_2$ and $R_4$ are fluoro.

13. The compound according to claim 1, wherein the compound of formula (I) is selected from the group consisting of compounds E0147, E0148, E0149, E1017, E1018, E1019, E1020, E1021, E1022, E1024, E1025, E1026, E1027, E1028, E1030, E1031, E1032, E1039, E1042, E1045, E1048 and E1051:

| Comp. No. | Chemical structure |
|---|---|
| E0147 | 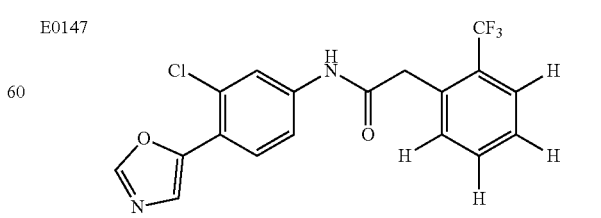 |

| Comp. No. | Chemical structure |
|---|---|
| E0148 | 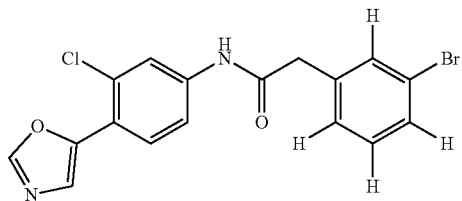 [SMILES: O=C(Cc1cccc(Br)c1)Nc1ccc(-c2cnco2)c(Cl)c1] |
| E0149 | 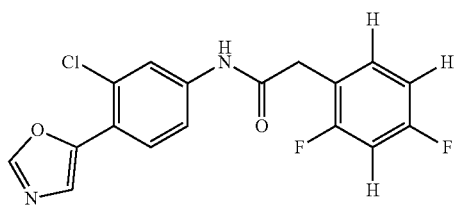 [SMILES: O=C(Cc1ccc(F)cc1F)Nc1ccc(-c2cnco2)c(Cl)c1] |
| E1017 | 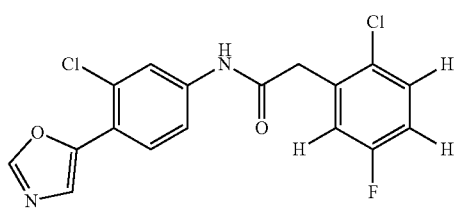 |
| E1018 | 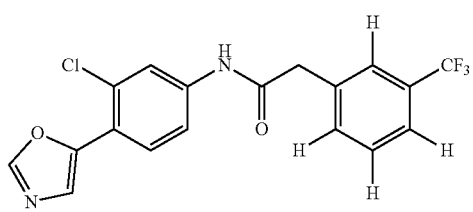 |
| E1019 | 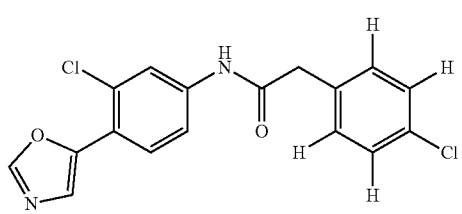 |
| E1020 | 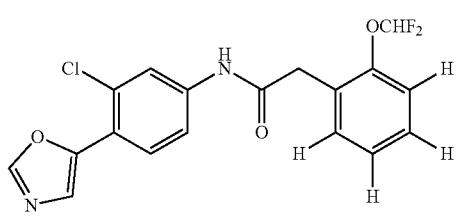 |
| E1021 | 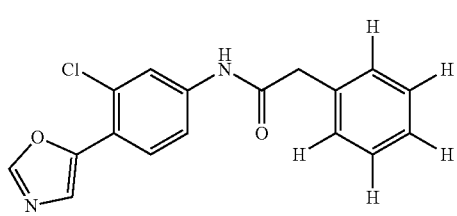 [SMILES: O=C(Cc1ccccc1)Nc1ccc(-c2cnco2)c(Cl)c1] |
| Comp. No. | Chemical structure |
|---|---|
| E1022 | 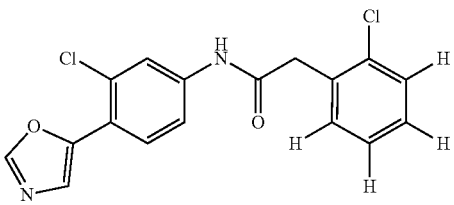 |
| E1024 | 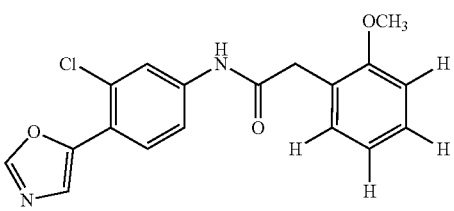 |
| E1025 | 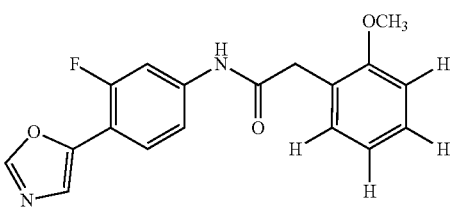 |
| E1026 | 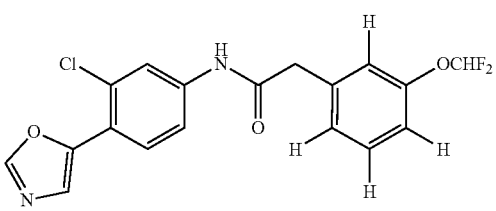 |
| E1027 | 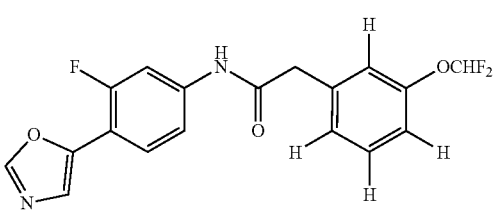 |
| E1028 | 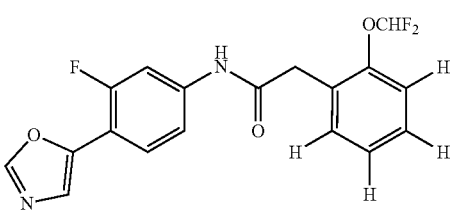 [SMILES: COc1ccccc1CC(=O)Nc1ccc(-c2cnco2)c(Cl)c1] |
| E1030 | 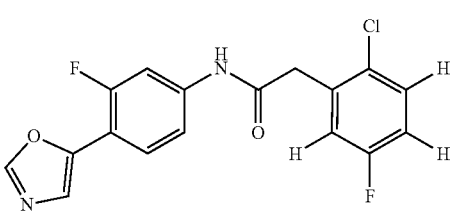 [SMILES: O=C(Cc1cc(F)ccc1Cl)Nc1ccc(-c2cnco2)c(F)c1] |

-continued

| Comp. No. | Chemical structure |
|---|---|
| E1031 | 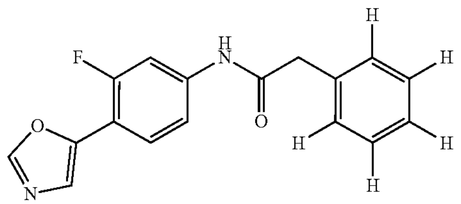 [SMILES: O=C(Cc1ccccc1)Nc1ccc(-c2cnco2)c(F)c1] |
| E1032 | 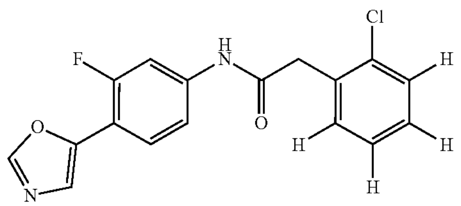 |
| E1039 | 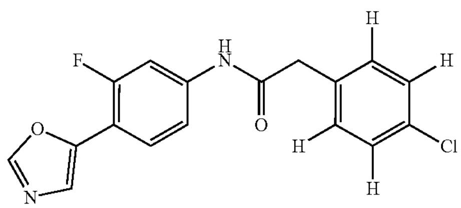 [SMILES: O=C(Cc1ccc(Cl)cc1)Nc1ccc(-c2cnco2)c(F)c1] |
| E1042 | 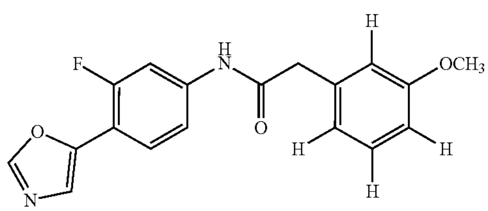 [SMILES: COc1cccc(CC(=O)Nc2ccc(-c3cnco3)c(F)c2)c1] |
| E1045 | 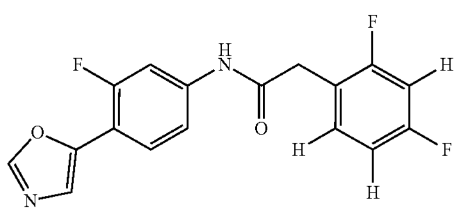 |
| E1048 | 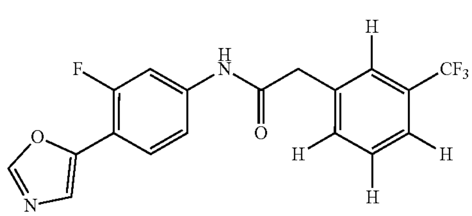 [SMILES: O=C(Cc1cccc(C(F)(F)F)c1)Nc1ccc(-c2cnco2)c(F)c1] |
| E1051 | 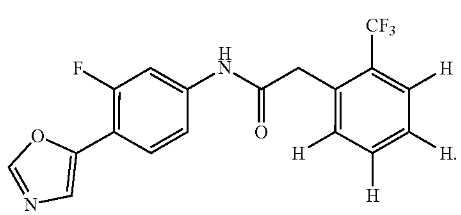 |

14. A pharmaceutical composition comprising a pharmaceutically acceptable carrier and/or adjuvant; and a compound of formula (Ia)

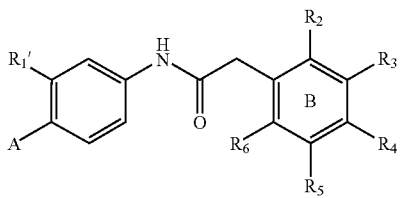

or a pharmaceutically acceptable salt thereof, wherein:

A is a 5-oxazolyl residue or a pyridine-4-yl residue;

$R_{1'}$ is selected from the group consisting of methoxy, hydrogen, fluoro and chloro;

$R_2$, $R_3$, $R_4$, $R_5$ and $R_6$ of the phenyl ring B are independently from each other selected from the group consisting of hydrogen, a linear or branched alkyl having 1 to 4 carbon atoms, trifluoromethyl, 2,2,2-trifluoroethyl, methylsulfanyl, ethylsulfanyl, methylsulfonyl, ethylsulfonyl, difluoromethoxy, trifluoromethoxy, fluoro, bromo, chloro, methoxy, ethoxy, propoxy, butoxy, hydroxy and amino; and at least two of $R_2$, $R_3$, $R_4$, $R_5$ and $R_6$ are hydrogens, with the proviso that if $R_{1'}$ is hydrogen or methoxy, A is a pyridine-4-yl residue, as a therapeutically active substance.

15. The pharmaceutical composition according to claim 14, wherein the compound of formula (Ia) is selected from the group consisting of compounds E0147, E0148, E0149, E1017, E1018, E1019, E1020, E1021, E1022, E1024, E1025, E1026, E1027, E1028, E1030, E1031, E1032, E1039, E1042, E1045, E1048 and E1051:

| Comp. No. | Chemical structure |
|---|---|
| E0147 | 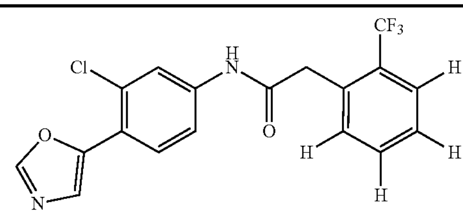 |
| E0148 | 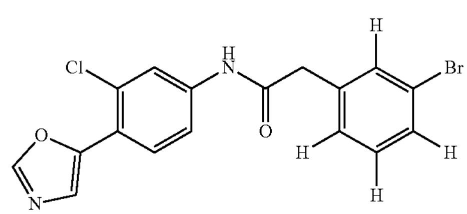 [SMILES: O=C(Cc1cccc(Br)c1)Nc1ccc(-c2cnco2)c(Cl)c1] |
| E0149 | 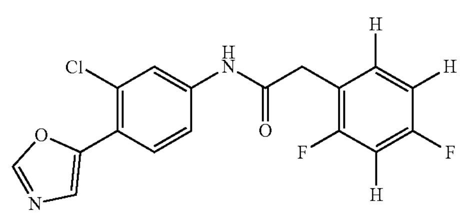 [SMILES: O=C(Cc1ccc(F)cc1F)Nc1ccc(-c2cnco2)c(Cl)c1] |

| Comp. No. | Chemical structure |
|---|---|
| E1017 | 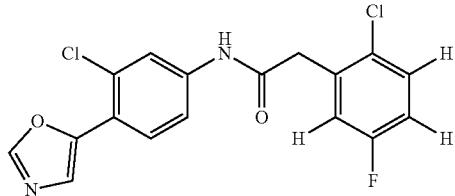 |
| E1018 | 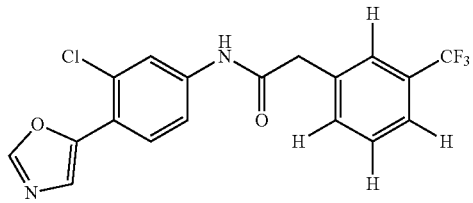 |
| E1019 | 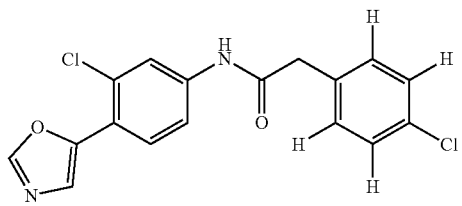 |
| E1020 | 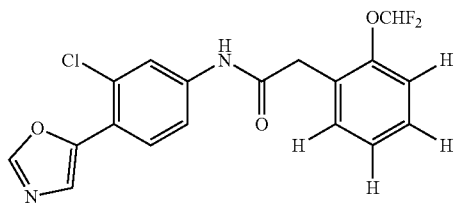 |
| E1021 | 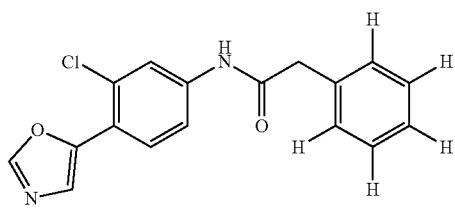 |
| E1022 | 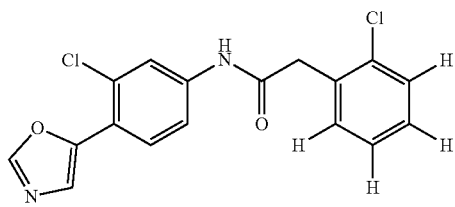 |
| E1024 | 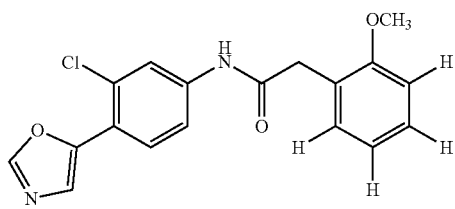 [SMILES: COc1ccccc1CC(=O)Nc1ccc(-c2cnco2)c(Cl)c1] |
| Comp. No. | Chemical structure |
|---|---|
| E1025 | 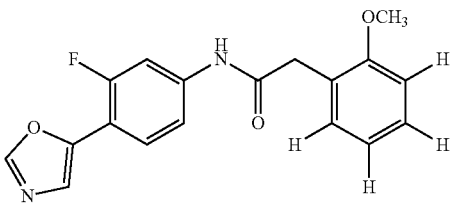 [SMILES: COc1ccccc1CC(=O)Nc1ccc(-c2cnco2)c(F)c1] |
| E1026 | 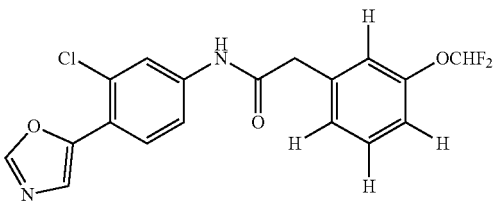 |
| E1027 | 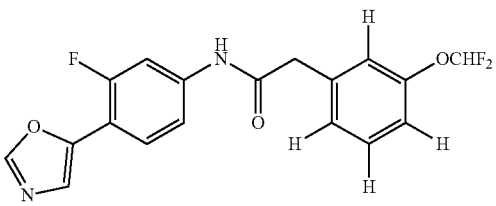 [SMILES: O=C(Cc1cccc(OC(F)F)c1)Nc1ccc(-c2cnco2)c(F)c1] |
| E1028 | 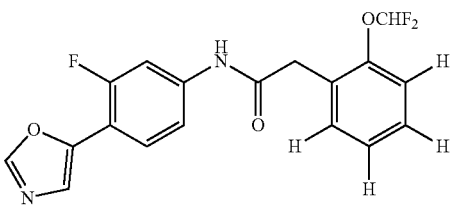 [SMILES: O=C(Cc1ccccc1OC(F)F)Nc1ccc(-c2cnco2)c(F)c1] |
| E1030 | 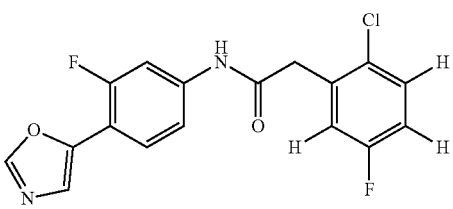 |
| E1031 | 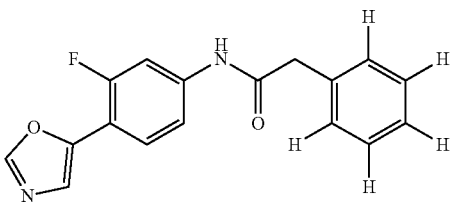 [SMILES: O=C(Cc1ccccc1)Nc1ccc(-c2cnco2)c(F)c1] |
| E1032 | 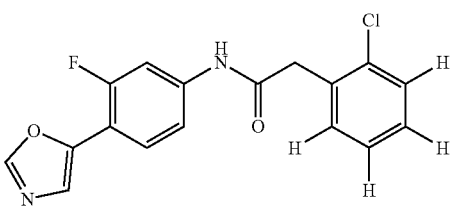 |

| Comp. No. | Chemical structure |
|---|---|
| E1039 | 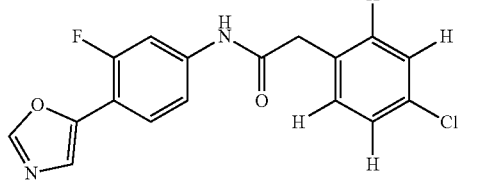 |
| E1042 | 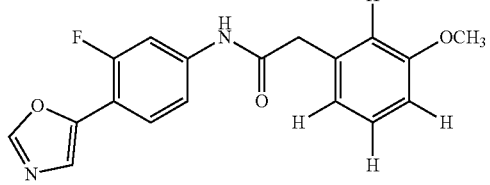 |
| E1045 | 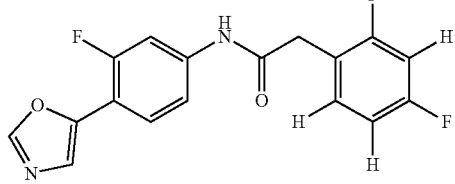 |
| E1048 | 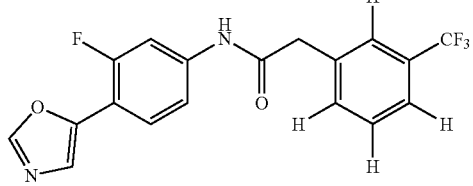 |
| E1051 | 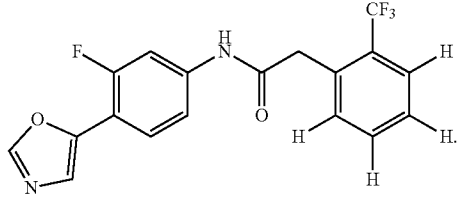 |
16. The pharmaceutical composition according to claim 14, wherein the compound of formula (Ia) is a compound selected from the group consisting of compounds E0147, E0148, E0149, E1017, E1018, E1019, E1020, E1021, E1022, E1024, E1025, E1026, E1027, E1028, E1030, E1031, E1032, E1039, E1042, E1045, E1048, E1051, E0027, E1060, E1062, E1063, E1066, E1068, E1069, E1070, E1071, E1072, E1073 and E1078:
E0147 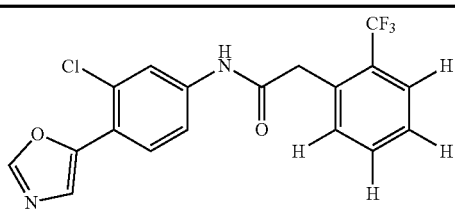
E0148 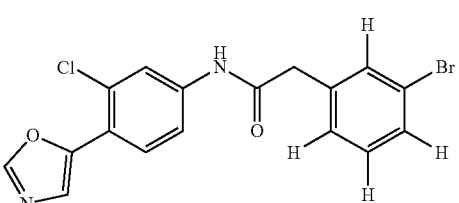
E0149 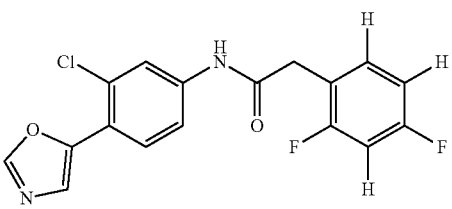
E1017 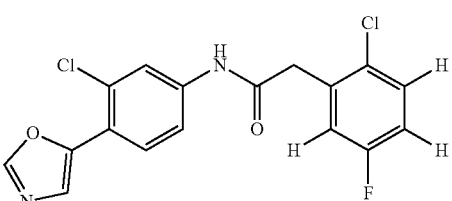
E1018 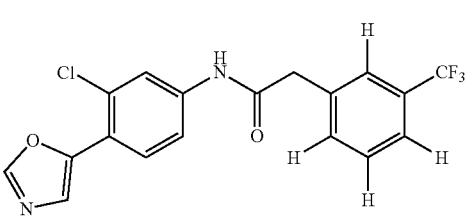 [SMILES: O=C(Cc1cccc(C(F)(F)F)c1)Nc1ccc(-c2cnco2)c(Cl)c1]
E1019 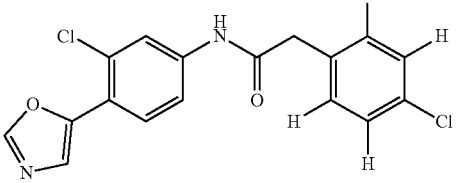
E1020 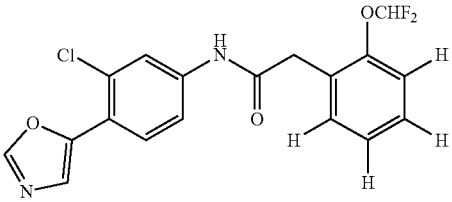 [SMILES: O=C(Cc1ccccc1OC(F)F)Nc1ccc(-c2cnco2)c(Cl)c1]
E1021 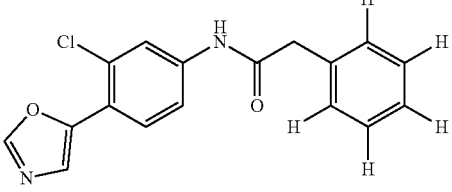

E1022 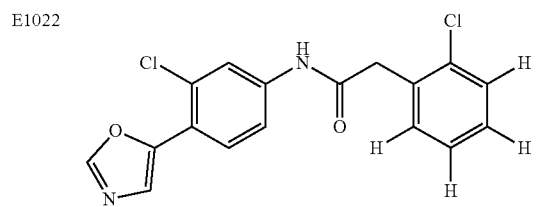
E1024 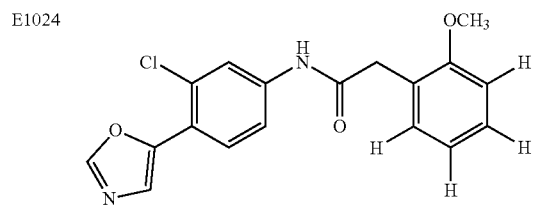
E1025 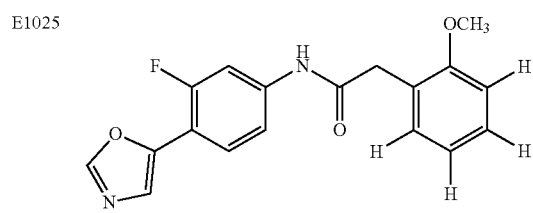
E1026 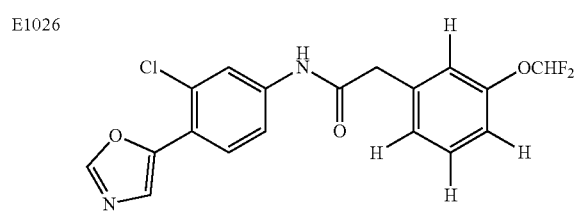
E1027 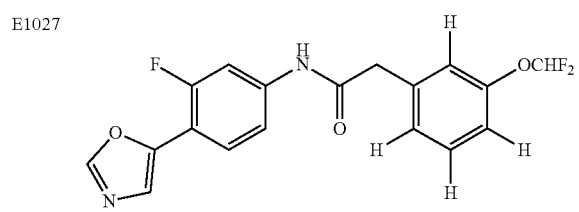
E1028 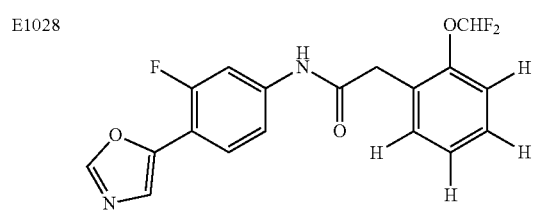
E1030 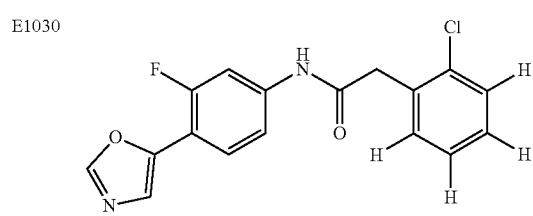
E1031 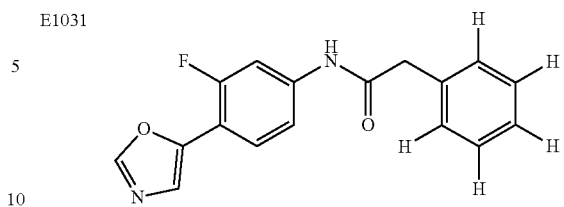
E1032 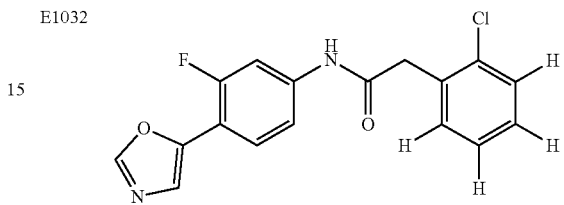
E1039 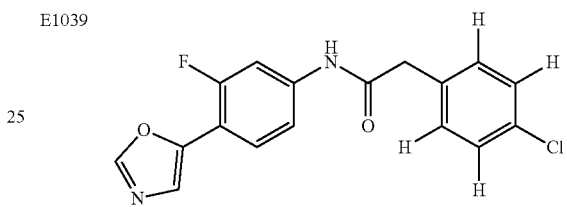
E1042 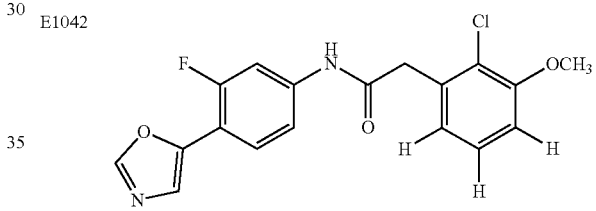
E1045 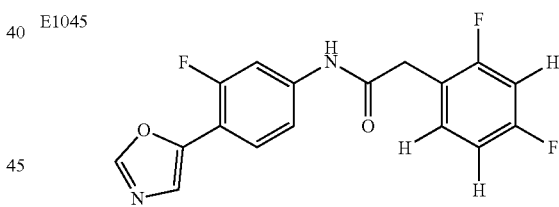
E1048 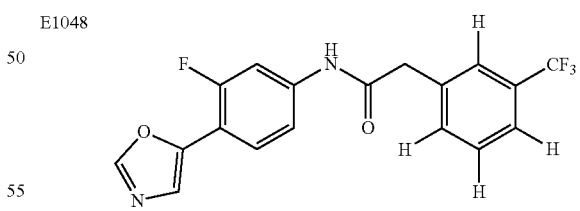
E1051 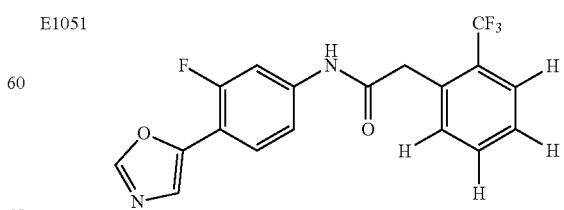

E0027 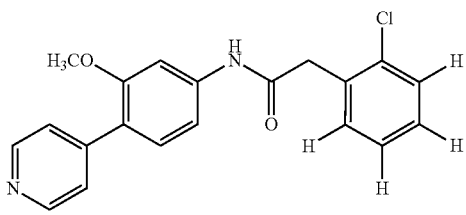

E1060 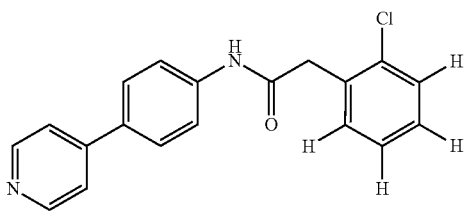 [SMILES: O=C(Cc1ccccc1Cl)Nc1ccc(-c2ccncc2)cc1]

E1062 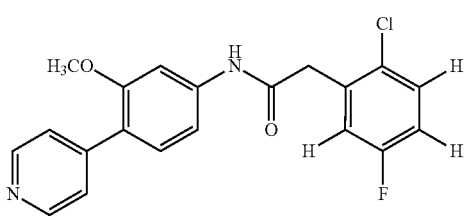

E1063 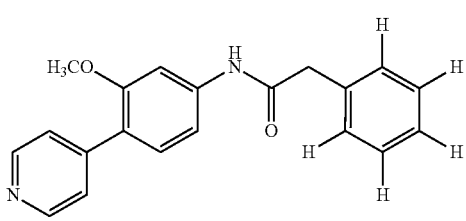

E1066 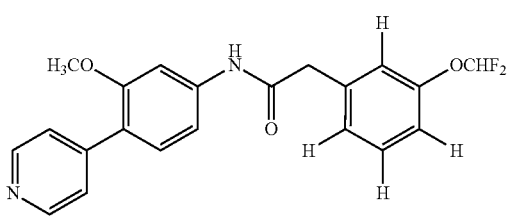 [SMILES: COc1cc(NC(=O)Cc2cccc(OC(F)F)c2)ccc1-c1ccncc1]

E1068 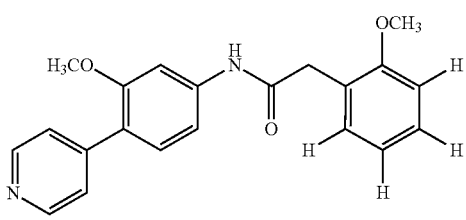

E1069 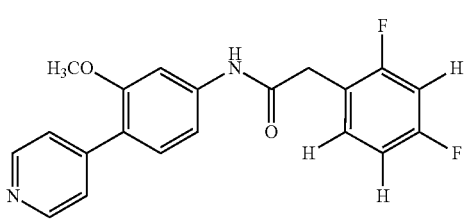 [SMILES: COc1cc(NC(=O)Cc2ccc(F)cc2F)ccc1-c1ccncc1]

E1070 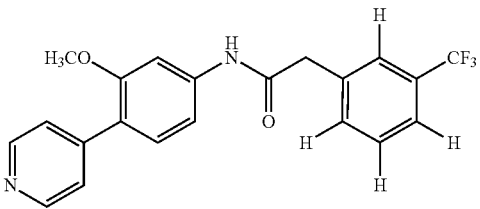 [SMILES: COc1cc(NC(=O)Cc2cccc(C(F)(F)F)c2)ccc1-c1ccncc1]

E1071 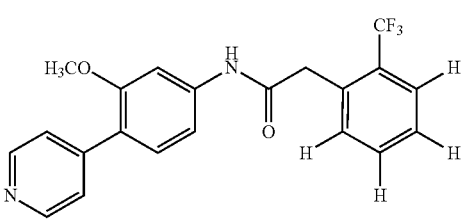

E1072 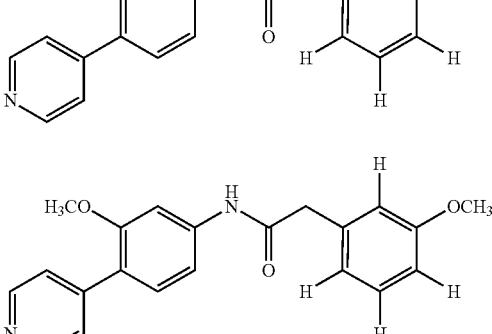

E1073 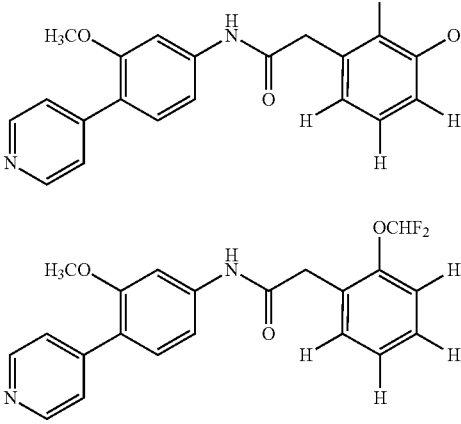

E1078 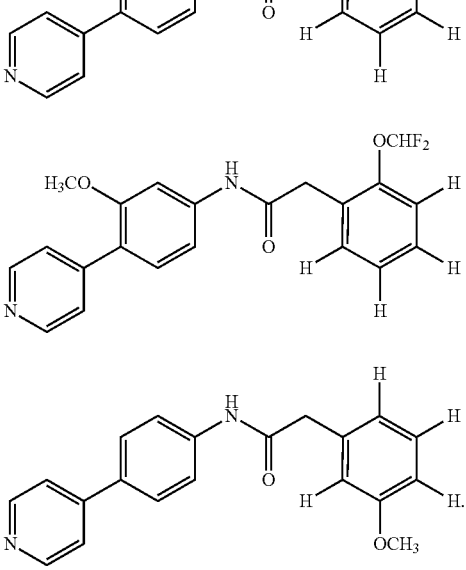

17. The pharmaceutical composition according to claim 14, comprising a pharmaceutically acceptable salt of the compound of formula (I).

18. The pharmaceutical composition according to claim 14, further comprising one or more additional therapeutic agents.

19. The pharmaceutical composition according to claim 14, wherein the pharmaceutical composition provides controlled release properties.

20. The pharmaceutical composition according to claim 14, wherein the pharmaceutical preparation is suitable for intraocular injection.

21. A method of treating a retinal disease that leads to photoreceptor loss or outer-retina degeneration, comprising administering a compound of formula (Ia) or a pharmaceutically acceptable salt thereof to a patient having the retinal disease so as to be delivered to an eye of the patient in an amount effective to treat the retinal disease:

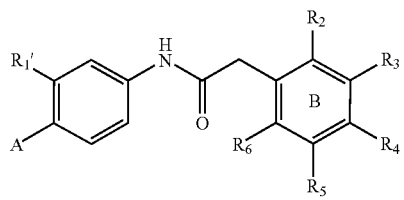

(Ia)

or a pharmaceutically acceptable salt thereof,
wherein:
A is a 5-oxazolyl residue or a pyridine-4-yl residue;
$R_{1'}$ is selected from the group consisting of methoxy, hydrogen, fluoro and chloro;
$R_2$, $R_3$, $R_4$, $R_5$ and $R_6$ of the phenyl ring B are independently from each other selected from the group consisting of hydrogen, a linear or branched alkyl having 1 to 4 carbon atoms, trifluoromethyl, 2,2,2-trifluoroethyl, methylsulfanyl, ethylsulfanyl, methylsulfonyl, ethylsulfonyl, difluoromethoxy, trifluoromethoxy, fluoro, bromo, chloro, methoxy, ethoxy, propoxy, butoxy, hydroxy and amino; and
at least two of $R_2$, $R_3$, $R_4$, $R_5$ and $R_6$ are hydrogens,
with the proviso that if $R_{1'}$ is hydrogen or methoxy, A is a pyridine-4-yl residue.

22. The method according to claim 21, wherein $R_{1'}$ is selected from the group consisting of fluoro, chloro and methoxy.

23. The method according to claim 21, wherein A is a 5-oxazolyl residue.

24. The method according to claim 21, wherein the phenyl ring B is monosubstituted.

25. The method according to claim 21, wherein $R_2$ is selected from the group consisting of methyl, trifluoromethyl, methylsulfanyl, methylsulfonyl, difluoromethoxy, fluoro, bromo, chloro, methoxy, and ethoxy.

26. The method according to claim 21, wherein $R_3$ or $R_4$ is selected from the group consisting of trifluoromethyl, difluoromethoxy, and methoxy.

27. The method according to claim 21, wherein the phenyl ring B is disubstituted.

28. The method according to claim 21, wherein $R_2$ is selected from the group consisting of fluoro, bromo, and chloro, and one of $R_3$, $R_4$ or $R_5$ is selected from the group consisting of fluoro, bromo, and chloro.

29. The method according to claim 21, wherein $R_2$ is chloro and $R_5$ is fluoro.

30. The method according to claim 21, wherein both $R_2$ and $R_4$ are fluoro.

31. The method according to claim 21, wherein the compound of formula (Ia) is selected from the group consisting of compounds E0147, E0148, E0149, E1017, E1018, E1019, E1020, E1021, E1022, E1024, E1025, E1026, E1027, E1028, E1030, E1031, E1032, E1039, E1042, E1045, E1048, E1051, E0027, E1060, E1062, E1063, E1066, E1068, E1069, E1070, E1071, E1072, E1073 and E1078:

E0146

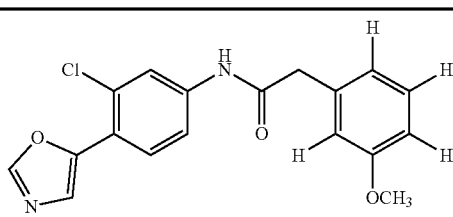

E0147

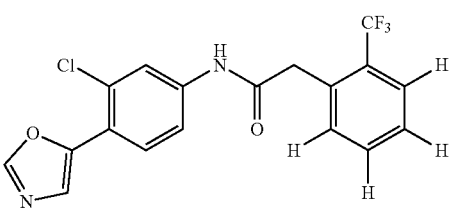 [SMILES: O=C(Cc1ccccc1C(F)(F)F)Nc1ccc(-c2cnco2)c(Cl)c1]

E0148

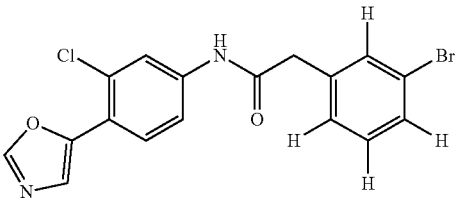 [SMILES: O=C(Cc1cccc(Br)c1)Nc1ccc(-c2cnco2)c(Cl)c1]

E0149

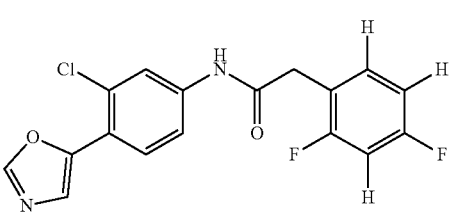 [SMILES: O=C(Cc1ccc(F)cc1F)Nc1ccc(-c2cnco2)c(Cl)c1]

E1017

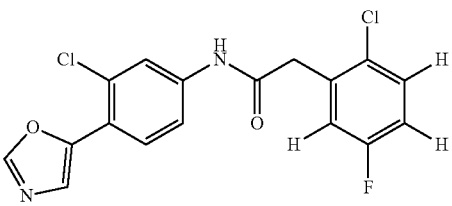 [SMILES: O=C(Cc1cc(F)ccc1Cl)Nc1ccc(-c2cnco2)c(Cl)c1]

E1018

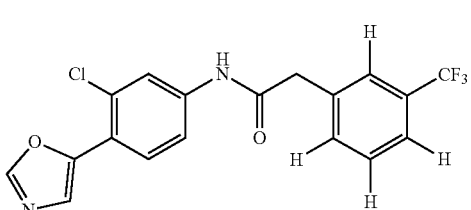

E1019

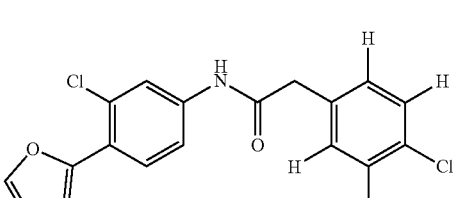

E1020

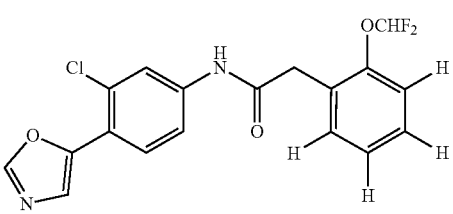

E1021 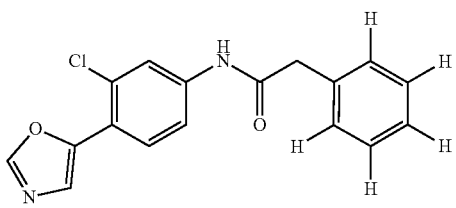
E1022 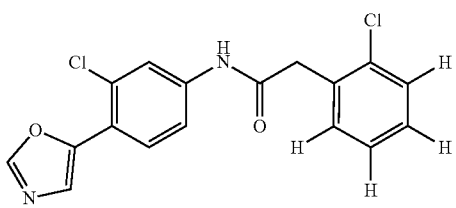 [SMILES: O=C(Cc1ccccc1)Nc1ccc(-c2cnco2)c(Cl)c1]
E1024 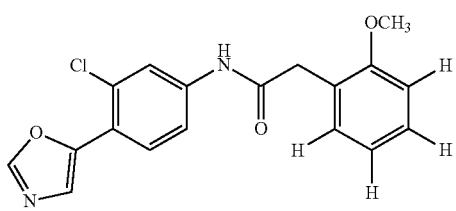
E1025 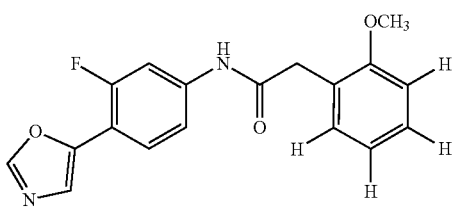
E1026 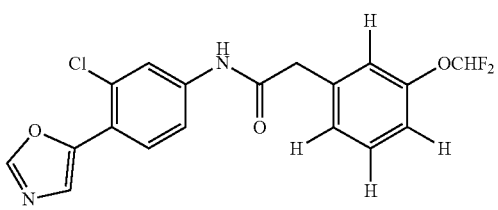 [SMILES: O=C(Cc1cccc(OC(F)F)c1)Nc1ccc(-c2cnco2)c(Cl)c1]
E1027 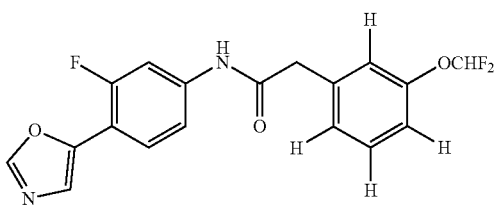 [SMILES: O=C(Cc1cccc(OC(F)F)c1)Nc1ccc(-c2cnco2)c(F)c1]
E1028 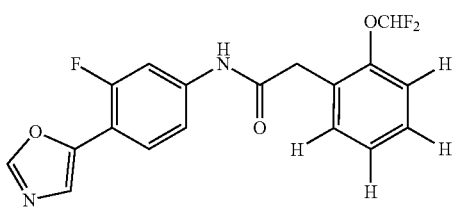 [SMILES: O=C(Cc1ccccc1OC(F)F)Nc1ccc(-c2cnco2)c(F)c1]
E1030 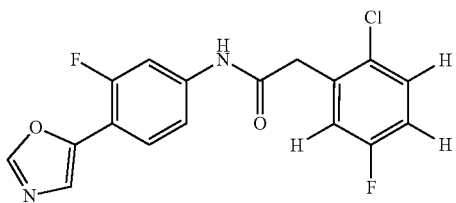
E1031 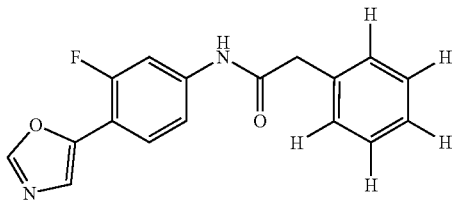
E1032 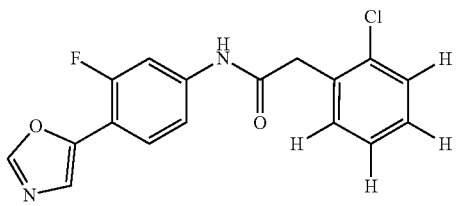
E1039 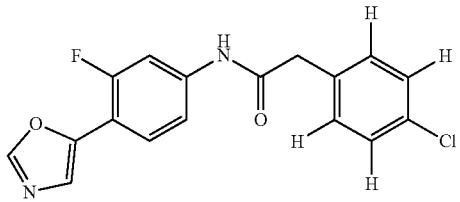 [SMILES: O=C(Cc1ccc(Cl)cc1)Nc1ccc(-c2cnco2)c(F)c1]
E1042 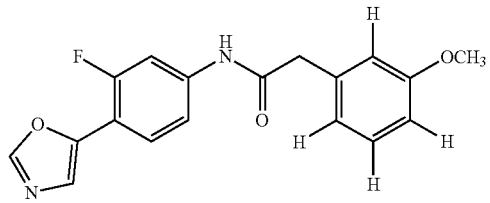 [SMILES: COc1cccc(CC(=O)Nc2ccc(-c3cnco3)c(F)c2)c1]
E1045 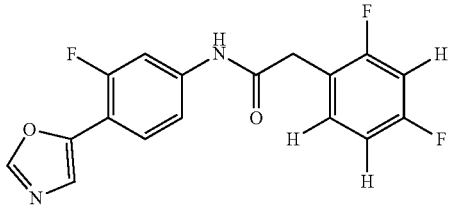 [SMILES: O=C(Cc1ccc(F)cc1F)Nc1ccc(-c2cnco2)c(F)c1]
E1048 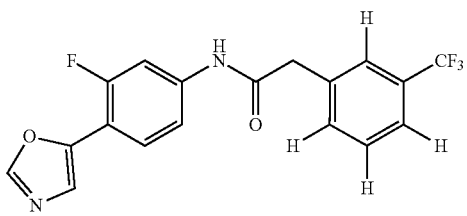 [SMILES: O=C(Cc1cccc(C(F)(F)F)c1)Nc1ccc(-c2cnco2)c(F)c1]

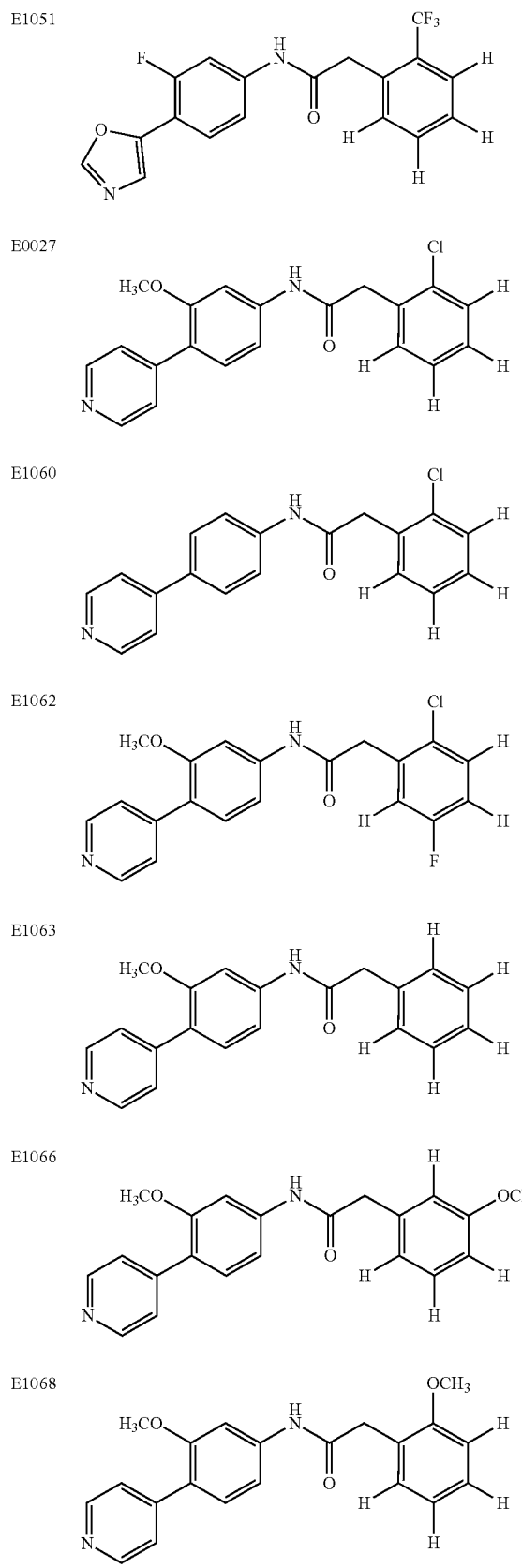
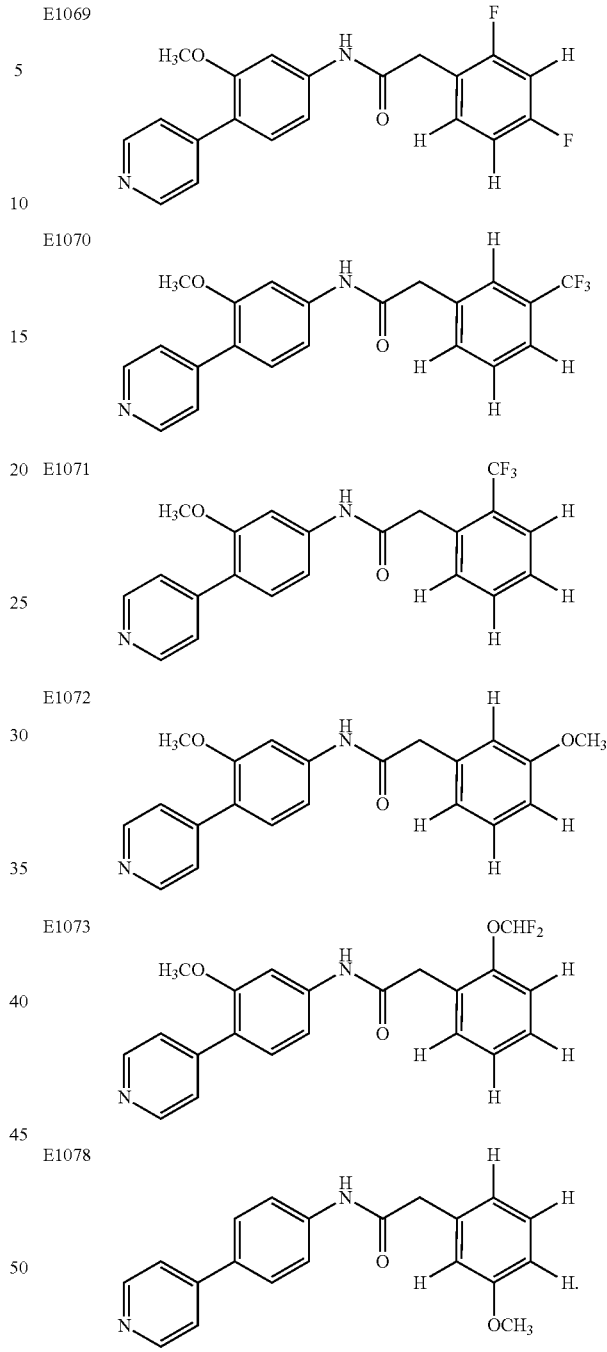

32. The method according to claim 21, wherein the compound of formula (Ia) or a pharmaceutically acceptable salt thereof is administered by intraocular injection.

33. The method according to claim 21, wherein retinal cells are regenerated via the proliferation of retinal precursor cells.

34. A method of inducing proliferation of retinal precursor cells comprising contacting retinal precursor cells with the pharmaceutical composition according to claim 14 so as to induce the proliferation of the retinal precursor cells.

35. The method according to claim 21, wherein the retinal disease is selected from the group consisting of inherited retinal dystrophies, acquired degeneration, vascular related retinal degeneration, drug-induced maculopathies, infectious eye diseases, inflammatory eye diseases and white dot syndromes, and wherein the pharmaceutical composition, upon administration, treats the retinal disease by inducing proliferation of retinal precursor cells.

36. The method according to claim 21, wherein the retinal disease is selected from the group consisting of retinitis pigmentosa (RP), including syndromic and non-syndromic forms, X-chromosome linked, recessive and dominant forms, rod-cone dystrophies, Usher's syndrome, Stargardt's disease, cone-rod dystrophies, cone dystrophies, achromatopsia, blue cone monochromacy, enhanced S-cone syndrome, rod dystrophies, choroideremia, Leber's congenital amaurosis, juvenile X-chromosome linked retinoschisis (JXLR), Best disease, Gyrate atrophy, fundus albipunctatus, retinitis punctata albescens, fleck retina of Kandori, bietti crystalline retinal dystrophy, North Carolina macular dystrophy, fenestrated sheen macular dystrophy, central areolar choroidal dystrophy (CACD), adult-onset foveomacular vitelliform dystrophy, Batten's disease, familial dominant drusen, congenital stationary night blindness, familial exudative vitreoretinopathy (FEVR), ocular albinism, oculocutaneous albinism, fovea hypoplasia, retinopathy of prematurity, abetalipoproteinemia, Stickler syndrome, retinal dystrophy (Bothnia type), dry age-related macular degeneration (dry AMD), wet age-related macular degeneration (wet AMD), geographic atrophy (GA), myopic degeneration, polypoidal choroidal vasculopathy (PCV), crystalline maculopathy (drug-related, hyperoxaluria, cystinosis, Sjogren-Larsson syndrome), west African crystalline maculopathy, solar retinopathy, talc retinopathy, diabetic retinopathy, sickle cell retinopathy, central serous retinopathy, macular telangectasia, angioid streaks, eales disease, retinal detachment, retinal dialysis, peripheral retinoschisis, central/branch retinal artery occlusion (CRAO/BRAO), central/branch retinal vein occlusion (CRVO/BRVO), haemorrhagic occlusive retinal vasculitis (HORV), drug-induced maculopathies including chloroquine, hydroxychloroquine, phenothiazine, quinine sulfate, thioridazine, clofazimine, cholopromazine, deferoxamine, chloroquine-derivatives, cisplatin, carmustine, chlofazimine and vigabatrin; crystal-induced maculopathies including tamoxifen, talc, canthaxanthine, methoxyflurane and nitrofurantoin; cystoid macular edema (CME) including epinephrine, latanoprost, nicotinic acid, progressive outer retinal necrosis (PORN), acute retinal necrosis (ARN), CMV-retinitis, Sarcoidosis, acute syphilitic posterior placoid chorioretinitis, tuberculosis chorioretinitis, toxoplasmic retinochoroiditis, Vogt-Koyanagi-Harada (VKH), posterior Uveitis and retinal vasculitis, intermediate uveitis, pars planitis+/−CME, enophthalmitis (anterior and/or posterior), posterior scleritis, masquerade syndromes, acute posterior multifocal placoid pigment epitheliopathy (APMPPE), relentless placoid chorioretinopathy (RPC), serpiginous choroiditis, multiple evanescence white dot syndrome (MEWDS), multifocal choroiditis and panuveitis (MCP), punctate inner choroidopathy (PIC), birdshot retinochoroidopathy, presumed ocular histoplasmosis syndrome (POHS), acute macular neuroretinopathy (AMN) and acute zonal occult outer retinopathy (AZOOR).

37. The method according to claim 21 wherein the retinal disease is inherited retinal dystrophies.

38. The method according to claim 21, wherein the retinal disease is retinitis pigmentosa (RP).

* * * * *